United States Patent
Kishida et al.

(10) Patent No.: US 6,337,993 B1
(45) Date of Patent: *Jan. 8, 2002

(54) BLOOD FLOW MEASURING APPARATUS

(75) Inventors: Nobuyoshi Kishida, Utsunomiya; Yasuyuki Numajiri, Kawasaki; Shigeaki Ono, Utsunomiya, all of (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/031,765

(22) Filed: Feb. 27, 1998

(30) Foreign Application Priority Data

Feb. 27, 1997 (JP) .............................. 9-058590
Feb. 27, 1997 (JP) .............................. 9-058591
Feb. 28, 1997 (JP) .............................. 9-062497

(51) Int. Cl.[7] .............................. A61B 3/10
(52) U.S. Cl. .................. 600/476; 351/221; 351/209
(58) Field of Search ................ 600/476, 310, 600/318, 407; 351/209–211, 215, 221; 606/4

(56) References Cited

U.S. PATENT DOCUMENTS

| | | | |
|---|---|---|---|
| 3,802,768 A | * | 4/1974 | Robinson et al. |
| 4,257,689 A | * | 3/1981 | Yancey |
| 4,830,483 A | | 5/1989 | Kohayakawa ............ 351/221 |
| 4,866,243 A | | 9/1989 | Sakane et al. ............ 219/121 |
| 5,106,184 A | | 4/1992 | Milbocker |
| 5,125,730 A | * | 6/1992 | Taylor et al. |
| 5,186,173 A | * | 2/1993 | Zuckerman |
| 5,630,179 A | | 5/1997 | Kishida .................... 396/18 |
| 5,751,396 A | * | 5/1998 | Masuda et al. |
| 5,757,461 A | * | 5/1998 | Kasahara et al. |
| 5,844,658 A | * | 12/1998 | Kishida et al. |
| 6,027,216 A | * | 2/2000 | Guyton et al. |
| 6,112,114 A | * | 8/2000 | Dreher |

FOREIGN PATENT DOCUMENTS

| | | |
|---|---|---|
| JP | 63-288133 | 11/1988 |
| JP | 7-31596 | 2/1995 |
| WO | WO 92/03084 | 3/1992 |

* cited by examiner

Primary Examiner—Marvin M. Lateef
Assistant Examiner—Shawna J Shaw
(74) Attorney, Agent, or Firm—Fitzpatrick, Cella, Harper & Scinto

(57) ABSTRACT

A blood flow measuring apparatus includes a system control unit that sends outputs for controlling the start and end of the measurement to optimum gain calculation units, which calculate the optimum gains of photomultipliers for receiving the light reflected from the eye fundus and the system control unit controls whether the optimum gains are outputted or not. Also, the optimum gain calculation unit respectively supply the system control units with outputs for monitoring whether the setting of the optimum gain has been completed or not, whereby the system control unit discriminates whether the photomultipliers have been set at the optimum gains.

9 Claims, 20 Drawing Sheets

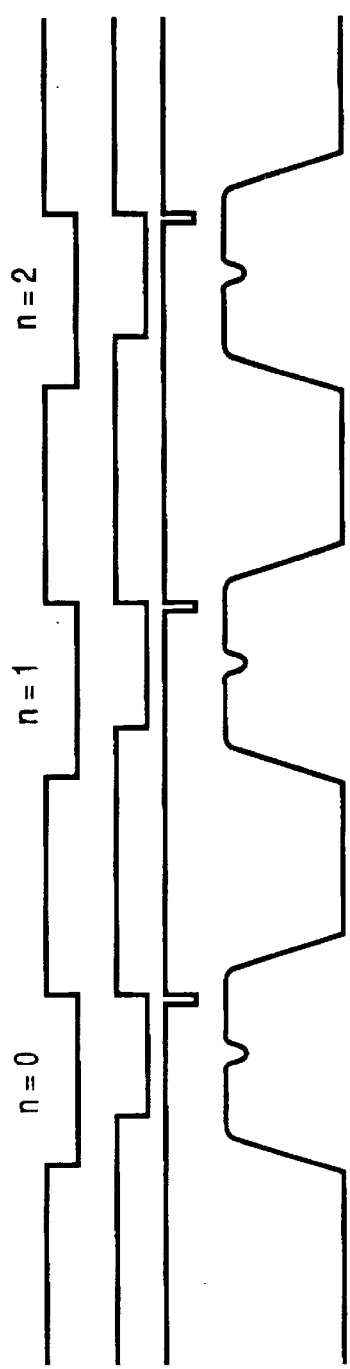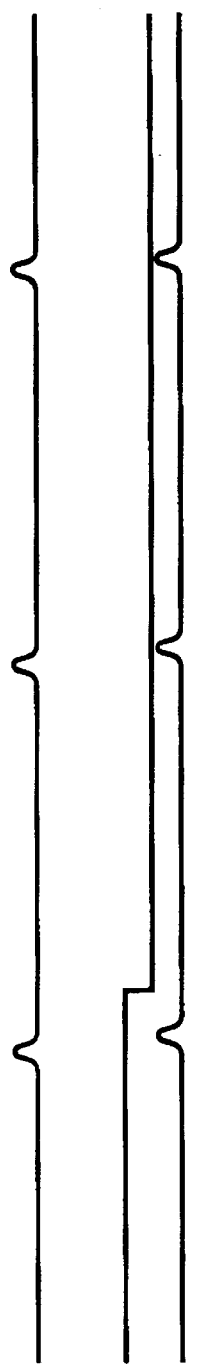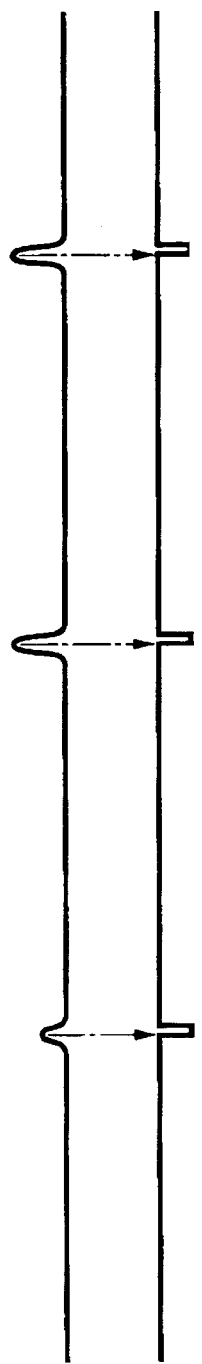

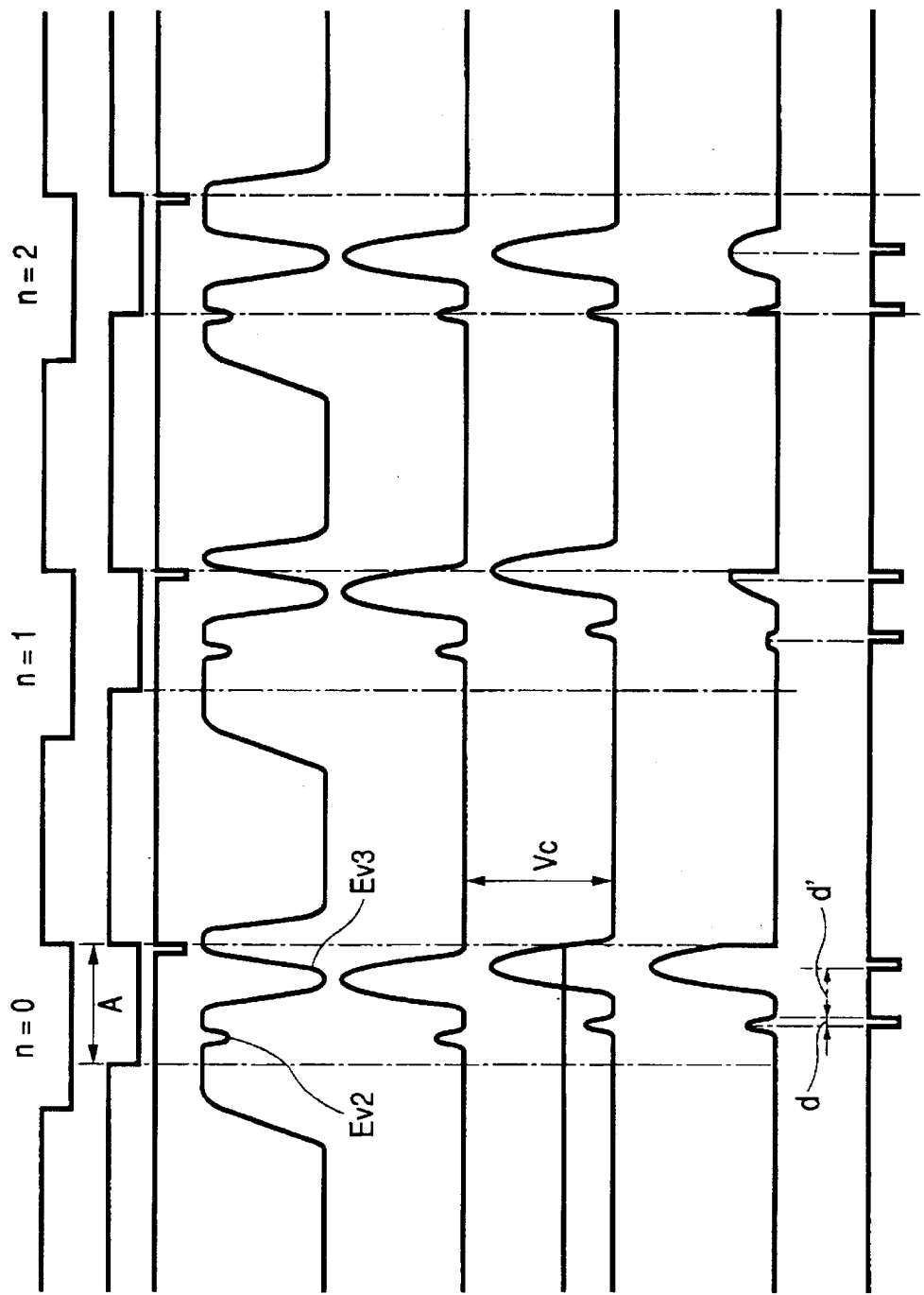

BLOOD FLOW MEASURING APPARATUS

BACKGROUND OF THE INVENTION

1. Field of the Invention

The present invention relates to an eye fundus blood flow meter for measuring the blood flow velocity, etc., in the blood vessels of the fundus.

2. Related Backfundus Art

There is already known a laser Doppler blood flow meter capable of tracking the vessel of the fundus of the eye to be examined and measuring the absolute blood flow velocity of the tracked vessel, and there is disclosed, for example in the Japanese Patent Laid-Open Application No. 7-031596, an apparatus for irradiating the vessel of the eye fundus with tracking laser light and laser light for measuring the blood flow velocity. In such an eye fundus blood flow meter, a reflected light, based on the laser light irradiating the eye fundus vessel for measuring the blood flow velocity and undergoing a Doppler shift caused by the blood cells flowing in the vessel, is received by a photomultiplier and the blood flow velocity is determined from the Doppler shift.

In such conventional apparatus, however, since the amount of the reflected light undergoing the Doppler shift varies significantly, for example, according to the position of the blood vessel on the eye fundus, the gain of the photomultiplier constituting the photosensor has to be adjusted frequently, each time the blood vessel to be measured is changed or the entering path of the measuring light is changed. For this reason, the eye to be examined is given an excessive amount of light by the operations of the examiner.

Also in the gain adjustment of the photomultiplier, the gain is adjusted to a maximum immediately before the start of the tracking operation since the received amount of light is very weak in this state, and, when the tracking operation is started, a large amount of light enters the photomultiplier at such a maximum gain, so that the deterioration of the photosensor is accelerated.

In the field of ophthalmic inspecting apparatus for tracking the movement of the blood vessels on the fundus of the eye to be examined, there are already known, for example, an apparatus for effecting two-dimensional tracking by detecting the vessel movement in two locations as disclosed in the Japanese Patent Laid-Open Application No. 63-288133, and an apparatus for effecting one-dimensional tracking by detecting, in one location, movement perpendicular to the direction of the blood vessel, as disclosed in the Japanese Patent Laid-Open Application No. 6-503733.

In such ophthalmic inspecting apparatus, a one-dimensional CCD is employed as the photosensor means for receiving the tracking light reflected on the eye fundus, and the tracking operation is achieved by calculating the amount of deviation between the tracking center position and the image position of the blood vessel by processing a signal indicating the blood vessel image. In such operation, in order to optimize the level of the blood vessel image signal, the gain of an amplifier is electrically regulated either manually or automatically, or the gain of an image intensifier positioned in front of the one-dimensional CCD is regulated in a similar manner to adjust the amount of light entering the one-dimensional CCD, in such a manner that the output signal level thereof lies within a predetermined range.

There is furthermore proposed an apparatus capable of tracking a moving object, by detecting the position thereof relative to a one-dimensional CCD and executing continuous feedback of the obtained position signal to image taking direction varying means which varies the image taking direction.

However the tracking in the above-mentioned conventional configurations, involving manual regulation of the gain of the amplifier for the one-dimensional CCD prior to the tracking operation or of the gain of the image intensifier for adjusting the light amount entering the one-dimensional CCD is cumbersome, requiring at least two operators. Besides it takes a long time, resulting in excessive light irradiation of the examinee. Also the tracking utilizing automatic regulation of the gain of the amplifier for the one-dimensional CCD prior to the tracking operation or of the gain of the image intensifier for adjusting the light amount entering the one-dimensional CCD, is less cumbersome in operation, but such automatic regulation is also conducted even while the examiner looks for the target position to be tracked, so that the entire operation is similarly time-taking, resulting again in the excessive light irradiation of the examinee.

Also in such conventional configurations, since the electrical regulation of the amplifier gain or the regulation of the gain of the light amount entering the one-dimensional CCD from the image intensifier is conducted in such a manner that a non-vessel light region on the eye fundus is not saturated, whereby the signal level for fine vessels of a low contrast becomes very small, hindering a satisfactory tracking operation.

Also in the actual measuring operation, the eye to be examined is not completely still but repeats fine movements even in the state of fixed gaze and the laser light has to follow such fine movements. However, in case of tracking a fine vessel with a low contrast which is positioned close to a large vessel with a high contrast, if the latter approaches to the center of tracking, for example, by the fine movement of the eyeball, the tracking may shift to the large vessel of the high contrast.

Furthermore, in the apparatus capable of tracking a moving object, there has not been disclosed a signal processing method for extracting the position of the vessel.

SUMMARY OF THE INVENTION

In consideration of the foregoing, a first object of the present invention is to provide an eye fundus blood flow meter that does not irradiate the eye fundus for an excessively long time, thereby reducing the burden to the eye to be examined.

A second object of the present invention is to provide an eye fundus blood flow meter which does not irradiate the photosensor means for an excessively long time, thereby enabling efficient use of the photosensor means for a prolonged period.

A third object of the present invention is to provide an ophthalmic apparatus not associated with the aforementioned drawbacks and capable of promptly and automatically regulating the gain of image taking means, thereby achieving measurement with a minimum light irradiation.

A fourth object of the present invention is to provide an ophthalmic inspecting apparatus not associated with the aforementioned drawbacks and capable of exact and stable tracking operation for a desired eye fundus blood vessel.

BRIEF DESCRIPTION OF THE DRAWINGS

FIGS. 18A, 18B, 18C, 18D, 18E, 18F, 18G, 18H and 18I are timing charts showing a tracking signal;

FIGS. 20A, 20B, 20C, 20D, 20E, 20F, 20G, 20H and 20I are timing charts showing a tracking signal;

DETAILED DESCRIPTION OF THE PREFERRED EMBODIMENTS

At first there will be explained an eye fundus blood flow meter comprising irradiation means for irradiating the blood vessel on the eye fundus with a laser light, photosensor means for receiving the laser light reflected by the eye fundus, and calculation means for starting a calculation for the optimum gain of the photosensor means in synchronization with the start of irradiation by the irradiation means.

Figure 1:
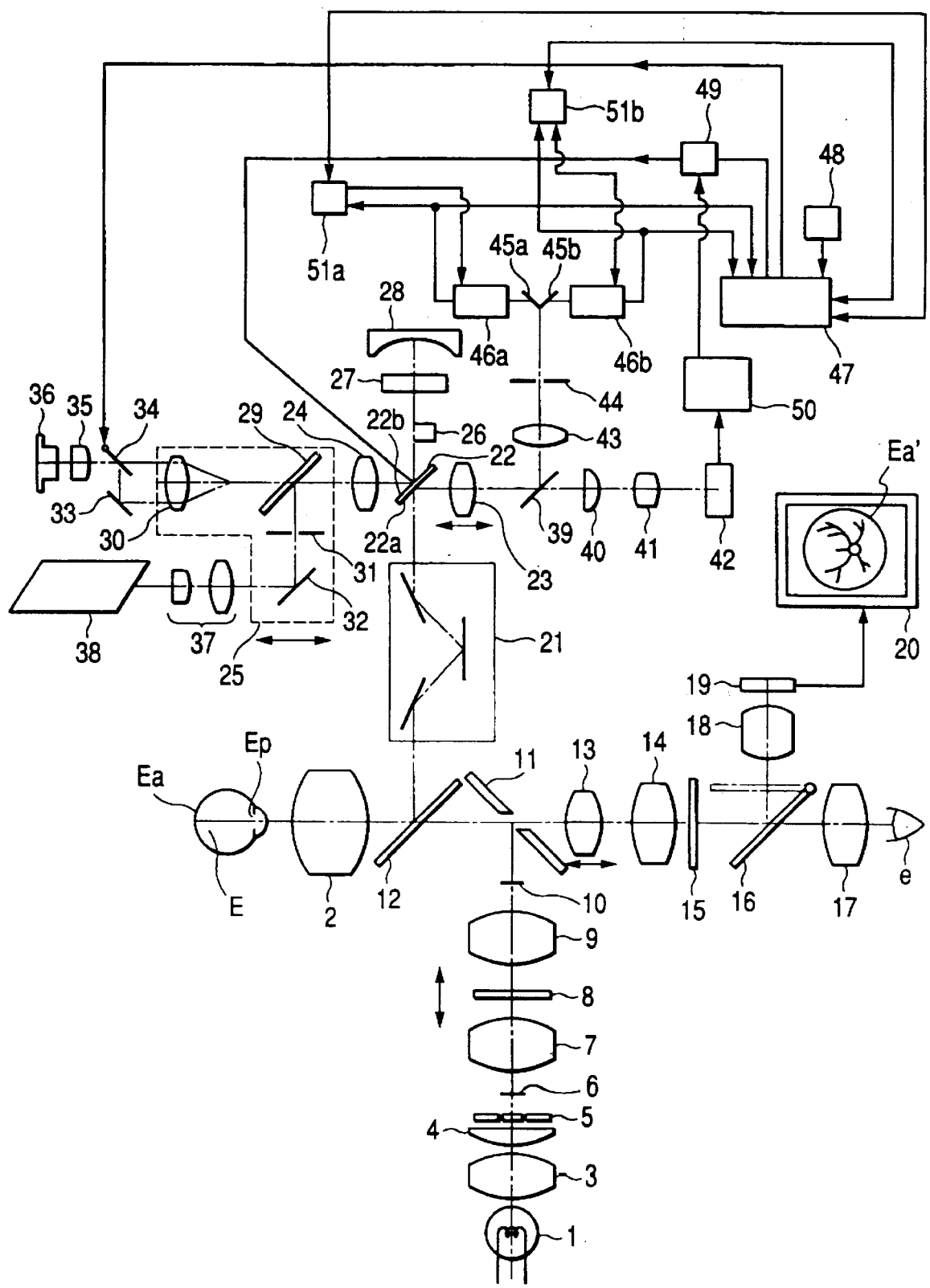
FIG. 1 is a view showing the configuration of an embodiment of the present invention.

FIG. 1 shows the configuration of an eye fundus blood flow meter constituting an embodiment of the present invention, in which, on an illumination optical path from an observation light source 1, composed for example of a tungsten lamp emitting white light, to an objective lens 2 opposed to an eye to be examined E, there are in succession provided a condenser lens 3, a field lens 4 with a band-pass filter transmitting, for example, only the yellow wavelength region, a ring slit 5 substantially conjugate with the pupil Ep of the eye to be examined E, a light shield member 6 substantially conjugate with the lens of the eye to be examined E, a relay lens 7, a transmissive liquid crystal plate 8 rendered movable along the optical path and serving as fixed index display element, a relay lens 9, a light shield member 10 conjugate with the vicinity of the cornea of the eye to be examined E, a holed mirror 11, and a band-pass filter 12 transmitting the light of a yellow wavelength region and reflecting the light of other wavelength regions, thereby constituting an eye fundus illuminating optical system. The ring slit 5 and the light shield members 6, 10 serve to separate the eye fundus illuminating light and the eye fundus observing light at the front eye region of the eye to be examined E, and the shape of these components is not critical as long as a suitable light shielding area can be formed.

Behind the holed mirror 11 there is provided an eye fundus observing optical system, which is provided, in succession in the path to the observing eye e, a focusing lens 13 movable along the optical path, a relay lens 14, a scale plate 15, an optical path switching mirror 16 insertable into and retractable from the optical path, and an eyepiece lens 17. In an optical path in the direction of reflection of the optical path switching mirror 16 when it is inserted into the optical path, there are provided a television relay lens 18 and a CCD camera 19 whose output is supplied to a liquid crystal monitor 20.

Also in an optical path in the direction of reflection of the band-pass filter 12 there are provided an image rotator 21 and a galvanometric mirror 22 polished on both faces and having a rotary axis perpendicular to the plane of the drawing, and in the direction of reflection of the lower reflective face 22a of the galvanometric mirror 22 provided is a second focus lens 23 movable along the optical path, while, in the direction of reflection of the upper reflective face 22b, there are provided a lens 24 and a focusing unit 25. The front focal plane of the lens 24 is conjugate with the pupil Ep of the eye to be examined E and the galvanometric mirror 22 is positioned on such a focal plane.

Behind the galvanometric mirror 22 there are provided an optical path length compensating semi-circular plate 26, a black spot plate 27 having a light shield region in the optical path, and a concave mirror 28 in a concentric manner on the optical axis, thereby constituting a relay optical system for guiding the light beam, which is not reflected by the lower reflective face 22a of the galvanometric mirror 22, to the upper reflective face 22b thereof.

The optical path length compensating semicircular plate 25 is provided to compensate for the aberration, in the vertical direction of the drawing, resulting from the thickness of the galvanometric mirror between the upper reflective face 22b and the lower reflective face 22a thereof, and functions only in the optical path toward the image rotator 21.

In the focusing unit 25 there are provided, on the same optical path of the lens 24, a dichroic mirror 29 and a condenser lens 30, and, on an optical path in the direction of reflection of the dichroic mirror 29 there are provided a mask 31 and a mirror 32. The focusing unit 25 is rendered integrally movable in a direction indicated by an arrow, along the optical path.

On an optical path at the entrance side of the condenser lens 30, there are provided a fixed mirror 33 and an optical path switching mirror 34 retractable from the optical path, and, on an optical path at the entrance side of the optical path switching mirror 34, there are provided a collimating lens 35 and a measuring laser diode 36 emitting coherent, light such as of a red color. Furthermore, on an optical path at the entrance side of the mirror 32 there are provided a beam expander 37 composed, for example, of a cylindrical lens, and a tracking light source 38 emitting light of a high intensity of a color, for example, green, different from that of the other light source.

On an optical path behind the second focusing lens 23, there are in succession provided a dichroic mirror 39, a field lens 40, a magnifying lens 41 and a one-dimensional CCD 42 with an image intensifier, thereby constituting a vessel detection system. Also on an optical path in the direction of reflection by the dichroic mirror 39, there are provided an imaging lens 43, a confocal diaphragm 44 and paired mirrors 45a, 45b substantially conjugate with the pupil Ep of the eye to be examined E, and, in the directions of reflection by the paired mirrors 45a, 45b there are respectively provided photomultipliers 46a, 46b to constitute measuring light receiving optical systems.

All the optical paths are illustrated on a same plane for the purpose of simplicity, but the optical path from the laser diode 36 to the mask 31, the measuring optical path at the exit side of the tracking light source 38 and the reflection optical paths of the paired mirrors 45a, 45b are in fact perpendicular to the plane of the drawing.

For controlling the entire apparatus there is provided a system control unit 47, to which are supplied the outputs of the photomultipliers 46a, 46b and the output of input means 48 to be operated by the examiner. The output of the system control unit 47 is supplied to the optical path switching mirror 34 and a galvanometric mirror control circuit 49 for controlling the galvanometric mirror 22, and the galvanometric control circuit 49 receives the output of the one-dimensional CCD 42 through a vessel position detecting circuit 50. Also the outputs of the photomultipliers 46a, 46b are respectively supplied to optimum gain calculating portions 51a, 51b whose outputs are supplied to the system control unit 47.

Figure 2:
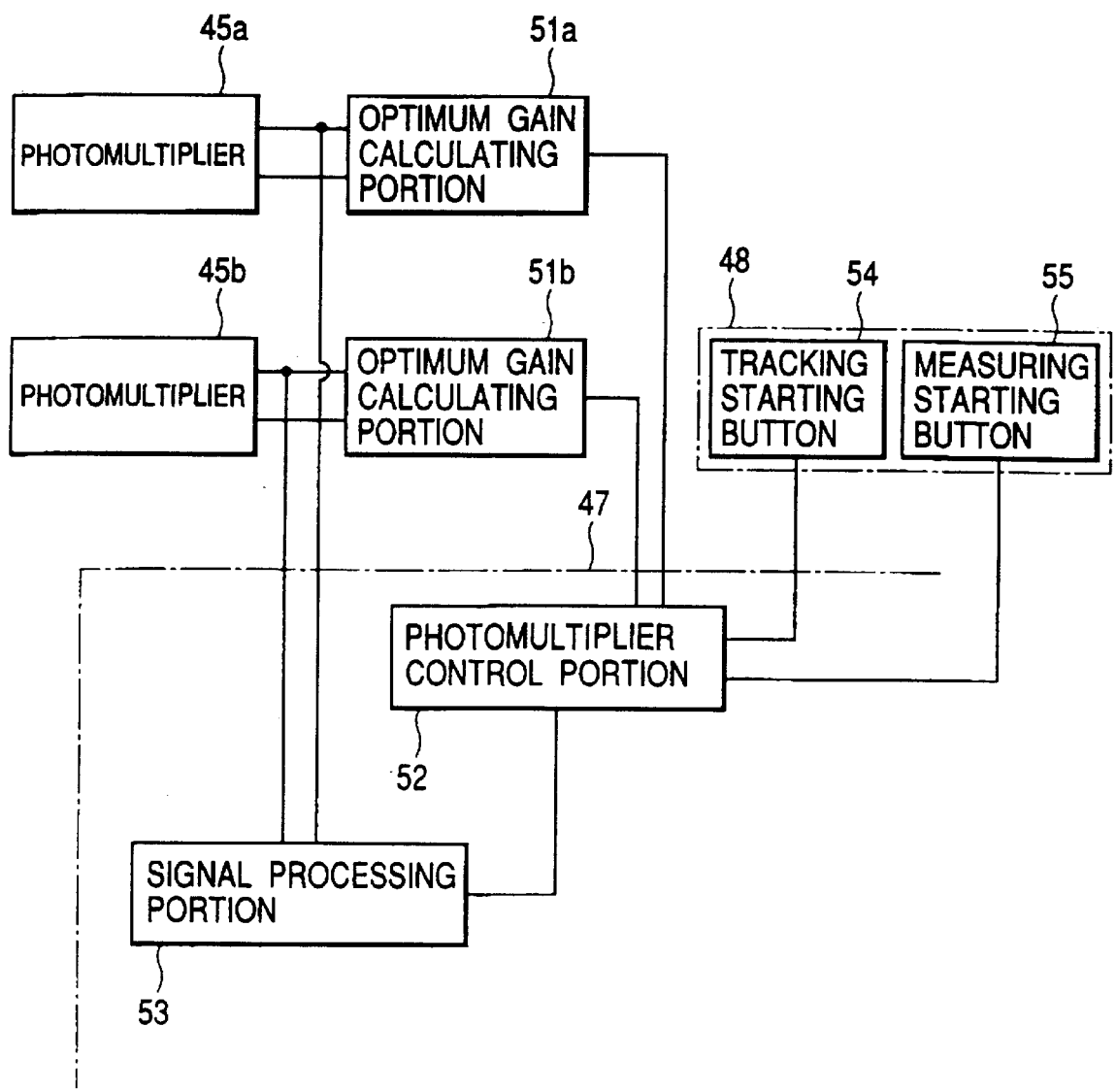
FIG. 2 is a view showing the configuration of a system control unit in the present invention.

FIG. 2 shows the internal configuration of the system control unit 47, which is provided therein with a photomultiplier control portion 52 and a signal processing portion 53. Other components will not be explained as they are not essential to the present invention. In the input means 48, the outputs of a tracking start button 54 and a measurement start button 55 are supplied to the photomultiplier control portion 52, whose outputs are supplied respectively to the photomultipliers 46a, 46b through the optimum gain calculating portions 51a, 51b. Also an output of the photomultiplier control portion 52 is supplied to the signal processing portion 53, whose outputs are supplied respectively to the photomultipliers 46a, 46b and the optical gain calculating portions 51a, 51b.

The white light emitted from the observing light source 1 is transmitted by the condenser lens 3. Then the light of yellow wavelength region only is transmitted by the field lens 4 with the band-pass filter, is further transmitted by the ring slit 5, the light shield member 6 and the relay lens 7, illuminates the transmissive liquid crystal plate 8 from the rear side, is further transmitted by the relay lens 9 and the light shield member 10, and is reflected by the holed mirror 11. Thus, the light of the yellow wavelength region only is transmitted by the band-pass mirror 12 and the objective lens 2 and is focused as an eye fundus illuminating light beam on the pupil Ep of the eye to be examined E, thus uniformly illuminating the eye fundus Ea. In this state the transmissive liquid crystal plate 8 displays a fixation target which is projected by the illuminating light onto the eye fundus Ea of the eye to be examined E and is presented thereto as a target image.

The light reflected by the eye fundus Ea returns on the same optical path and is taken out, from the pupil Ep, as an eye fundus observing light beam, which is guided through the central hole of the holed mirror 11, the focusing lens 13, and the relay lens 14, is then focused as an eye fundus image Ea' by the scale plate 15 and reaches the optical path switching mirror 16. When the optical path switching mirror 16 is retracted from the optical path, the observing eye e can observe the eye fundus image Ea' through the eyepiece lens 17, but, when the optical path switching mirror 16 is inserted into the optical path, the eye fundus image Ea' focused on the scale plate 15 is refocused on the CCD camera 19 through the television relay lens 18 and is displayed on the liquid crystal monitor 20.

The alignment of the apparatus is made under the observation of the eye fundus image Ea' either through the eyepiece lens 17 or the liquid crystal monitor 20. In this operation it is desirable to select the appropriate observing method according to the desired purpose. The observation through the eyepiece lens 17, being generally higher in the resolving power and in the sensitivity than the observation by the liquid crystal monitor 20, is suitable for diagnosis by reading delicate changes on the eye fundus Ea. On the other hand, the observation through the liquid crystal monitor 20 is also very useful for clinical purposes since such observation, not limited in the viewing field, can reduce the fatigue of the examiner and allows electronic recording of the successive changes in. the measured region of the eye fundus image Ea' by supplying the output of the CCD camera 19 to an external video cassette recorder or an external video printer.

The measuring light, emitted from the laser diode 36, is collimated by the collimating lens 35 and, if the optical path switching mirror 34 is inserted in the optical path, is reflected by this mirror 34 and the fixed mirror 33 to pass through the lower part of condenser lens 30, but, if the optical path switching mirror 34 is retracted from the optical path, it directly passes through the upper part of condenser lens 30, thus being transmitted by the dichroic mirror 29.

On the other hand, the tracking light emitted from the tracking light source 38 is expanded in beam diameter with different magnifications in the vertical and horizontal directions by the beam expander 37, then is reflected by the mirror 32, is shaped into a desired shape by the shaping mask 31, is further reflected by the dichroic mirror 29 and is superposed by the condenser lens 30 with the measuring light, which is focused into a spot at a position conjugate with the center of the aperture of the mask 31. The measuring light and the tracking light, mutually superposed, are transmitted by the lens 24, reflected by the upper reflective face 22b of the galvanometric mirror 22, transmitted by the black spot plate 27, reflected by the concave mirror 28, again transmitted by the black spot plate 27 and the optical path length correcting semicircular plate 26, and are returned toward the galvanometric mirror 22.

By the function of the relay optical system, which forms the image of the upper reflective face 22b and the lower reflective face 22a of the galvanometric mirror 22 with a magnification of −1, the measuring light and the tracking light reflected by the upper reflective face 22b are returned to the galvanometric mirror 22 in a state deviated from the optical axis of the objective lens 2, so that these lights are transmitted by the galvanometric mirror 22 without being reflected by the lower reflective face 22b thereof, further by the image rotator 21, then deflected by the band-pass filter 12 toward the objective lens 2 and projected therethrough to the eye fundus Ea of the eye to be examined E.

The light scattered and reflected at the eye fundus Ea is condensed by the objective lens 2, then is reflected by the band-pass filter 12, is transmitted by the image rotator 21, reflected by the lower reflective face 22a of the galvanometric mirror 22, and transmitted by the second focusing lens 23, and the measuring light and the tracking light are separated by the dichroic mirror 39.

The tracking light is transmitted by the dichroic mirror 39, and is focused by the field lens 40 and the imaging lens 41 on the one-dimensional CCD 42 as a vessel image which is magnified greater than the eye fundus image Ea' formed by the eye fundus observing optical system. Based on the vessel image taken by the one-dimensional CCD, the vessel position detection circuit 50 prepares data indicating the amount of displacement of the vessel image for supply to the control circuit 49, which drives the galvanometric mirror 22 so as to compensate for such an amount of displacement.

On the other hand, the measuring light is reflected by the dichroic mirror 39, is then transmitted by the aperture of the confocal diaphragm 44, reflected into two directions by the paired mirrors 45a, 45b and received by the photomultipliers 46a, 46b, whose output signals are supplied to the system control unit 47 and are subjected to a frequency analysis to determine the blood flow velocity at the eye fundus Ea.

The outputs of the photomultipliers 46a, 46b are also supplied to the optimum gain calculating portions 51a, 51b for calculating the optimum gains, which are respectively fed back to the photomultipliers 46a, 46b.

When the tracking start button 54 of the input means 48 is depressed, the photomultiplier control portion 52 of the system control unit 47 sends a calculation start signal to the optimum gain calculating portions 51a, 51b, which in response, calculates the optimum gains of the photomultipliers 46a, 46b and sends these optimum gains to the photomultipliers 46a, 46b.

The optimum gain calculation portions 51a, 51b monitor whether the photomultipliers 46a, 46b are set at the optimum gains, and send gain setting signals to the photomultiplier control portion 52, which therefore can know whether the photomultipliers 46a, 46b are set at the optimum gains.

As the time required for setting the photomultipliers 46a, 46b at the optimum gains is in the order of several hundred milliseconds, such setting can be normally achieved within a time from the depression of the tracking start button 54 to the depression of the measurement start button 55.

Then, when the measurement start button 55 is depressed, the photomultiplier control portion 52 sends a calculation stop signal to the optimum gain calculating portions 51a, 51b and simultaneously sends a process start signal to the signal processing portion 53, whereby the optimum gain calculating portions 51a, 51b terminate the calculation, while the signal processing portion 53 executes a process for determining the blood flow velocity.

In case the setting of the photomultipliers 46a, 46b at the optimum gains cannot be completed within the time from the depression of the tracking start button 54 to the depression of the measurement start button 55, the measurement is started after such setting is completed.

The calculation of the optimum gain is terminated at the start of measurement, but it may be continued thereafter. Also, as the optimum gain calculating portions 51a, 51b are independently operable, the calculation may be terminated when each of the photomultipliers 46a, 46b reaches the optimum gain after the start of tracking. Also the calculation of the optimum gain is started at the start of tracking, but it may be started at the start of measurement.

When the tracking start button 54 of the input means 48 is depressed, a tracking start signal is supplied to the system control unit 47, which in response sends an optimum gain calculation start signal to the optimum gain calculating portions 51a, 51b and then monitors optimum gain setting completion signals therefrom. Confirming the reception of the optimum gain setting completion signals, the system control unit 47 sends a galvanometric mirror drive signal to the galvanometric mirror control circuit 49. Also, the vessel position detection circuit 50 prepares and outputs data, representing the amount of displacement of the vessel image, to the galvanometric mirror control circuit 49, which in response drives the galvanometric mirror 22 so as to compensate for the amount of displacement, whereby the vessel on the eye fundus Ea is tracked.

When the examiner depresses the measurement start button 55 of the input means 48 after confirming the state of tracking, the input means 48 sends a measurement start signal to the system control unit 47, which determines the blood flow velocity by analyzing the Doppler signals from the photomultipliers 46a, 46b. In this state, the gains of the Doppler signals therefrom, tracking the same vessel, are adjusted to the optimum gains.

Also in case of measuring the blood flow velocity of the vessel of a different position of the same person or the blood flow velocity of the vessel of a different person, the measurement can be executed by determining the vessel to be measured and setting the optimum gains at the start of tracking in a similar manner. Consequently the examiner can execute the measurement without paying attention to whether the photomultipliers 46a, 46b are set at the optimum gains, and the loads on and deterioration of the photomultipliers 46a, 46b can therefore be reduced, in comparison with the case where the optimum gains for the photomultipliers 46a, 46b are constantly determined. Also, the operation of the examiner for determining the optimum gains for the photomultipliers 46a, 46b causes an additional light irradiation of the eye to be examined E, but the present embodiment can reduce the damage to the eye to be examined E.

Figure 3:
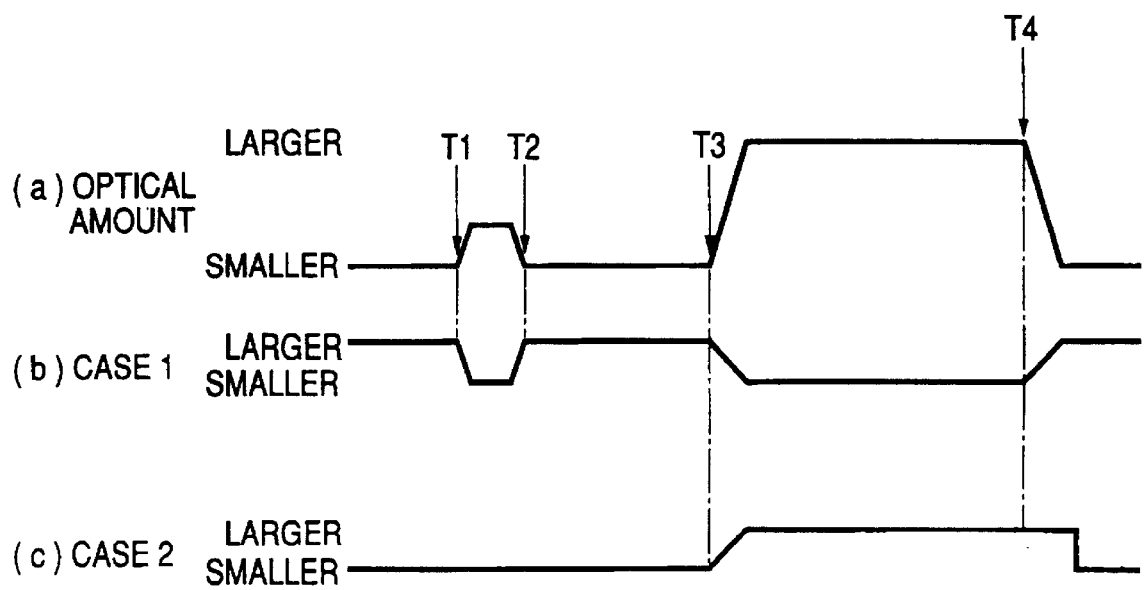
FIGS. 3 and 4 are timing charts showing an optimum gain setting operation of the present invention.

FIG. 3 is a timing chart, in which (a) indicates the incident light amount on the photomultipliers 46a, 46b, and which compares a case 1(b) of constantly setting the optimum gains for the photomultipliers 46a, 46b and a case 2(c) of setting the optimum gains at the start of the tracking operation as in the present embodiment.

In a period T1–T2, if light other than the Doppler shift light enters the photomultipliers 46a, 46b, the gain varies so as to attain an optimum gain in the case 1 in which the optimum gain is constantly determined, but the gain does not change in the case 2 in which the optimum gain is determined prior to the start of the tracking operation. Consequently, case 1 executes the gain setting more frequently than in case 2, whereby the loads to the photomultipliers 46a, 46b increase. Also, in the case 1, the gain is set at a maximum immediately before the start of the tracking operation at T3 because the light amount is very weak, and the photomultipliers 46a, 46b receive a large amount of light in a stage of maximum gain at T3, and this is undesirable for the photomultipliers 46a, 46b. On the other hand, in the case 2, the gain is set at a minimum at the end T4 of the measurement and maintained at this level unit the tracking operation is started at T3.

Consequently, the present embodiment allows use of the photomultipliers 46a, 46b in an efficient manner, over a prolonged period.

Figure 4:
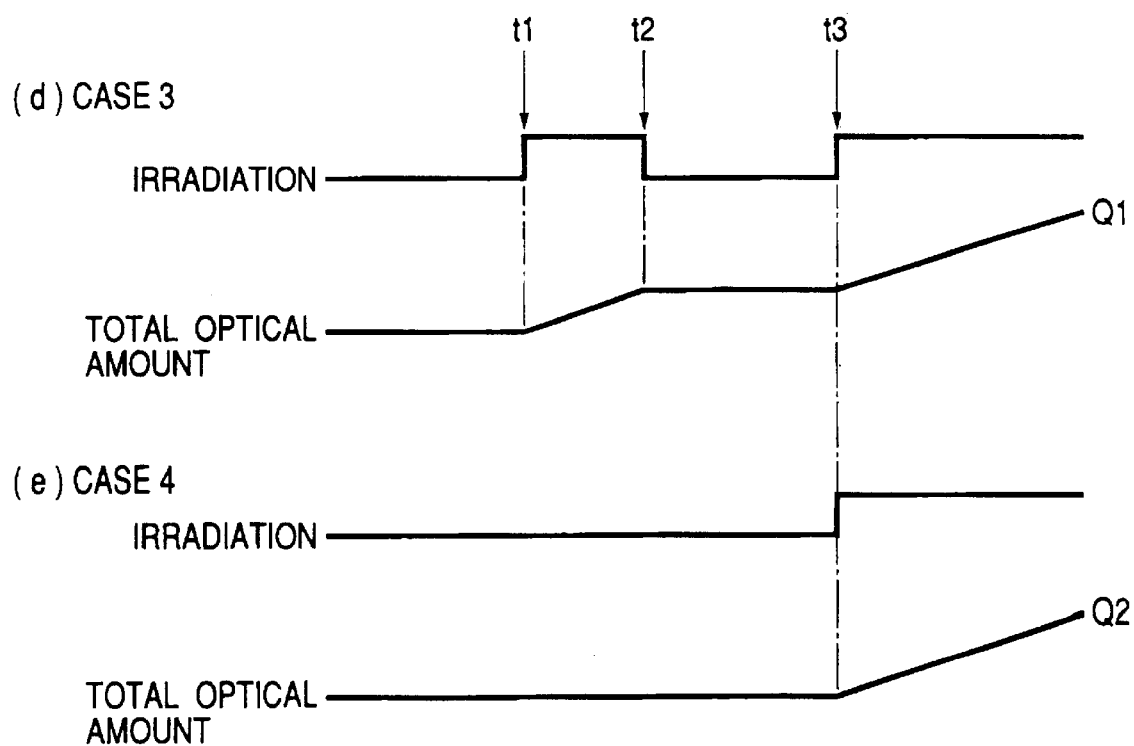

FIG. 4 is a timing chart comparing a case 3(d) in which the optimum gains for the photomultipliers 46a, 46b are set by the examiner, and a case 4(e) in which the optimum gains are automatically determined. The chart shows the timing of entry of the measuring light into the eye to be examined E, and the total light amount Q1 or Q2 indicates the total sum of the light amount entering into the eye to be examined E.

In the case 3 in which the examiner sets the optimum gains, the examiner sets the optimum gains for the photomultipliers 46a, 46b under the same conditions as in the measurement in the period from t1 to t2, so that the measuring light enters the eye to be examined E during this period. On the other hand, in the case 4 in which the optimum gains are determined at the start of tracking, the examiner is not required to set the optimum gains for the photomultipliers 46a, 46b under the same conditions as in the measurement in the period from t1 to t2, and the optimum gains are set simultaneously with the start of tracking at t3. Consequently, in comparison with the foregoing case 3, the eye to be examined E can be prevented from the entry of the measuring light in the unnecessary period.

Therefore, the present embodiment does not irradiate the eye to be examined E with the measuring light in the unnecessary period, there by reducing the burden on the eye to be examined E.

As explained in the foregoing, the eye fundus blood flow meter of the present invention can determine the optimum gains of the light receiving means immediately before the measuring operation, by starting the calculation of the optimum gain in synchronization with the s tart of irradiation, thereby exactly determining the blood flow velocity in the eye fundus Ea and reducing the light irradiating time to the eye to be examined Also, since the eye fundus blood flow meter of the present invention starts the calculation of the optimum gains in synchronization with the start of tracking, it need not execute the gain calculation for the light receiving means in a continuous manner, thereby reducing the damage thereto.

In the following there will be explained an apparatus comprising illumination means for illuminating an eye fundus area including a specified target region; detection means for detecting the light from such specified region; tracking means for executing a tracking operation following the movement of the eye fundus, utilizing the detection signal of the detection means; tracking start input means for outputting an input signal for starting the tracking of the tracking means; amplification gain determination means for determining the amplification gain of the detection means, based on an output signal therefrom; and control means for executing, in succession, a first step for causing the amplification gain determination means to determine the amplification gain of the detection means in response to the input signal from the tracking start input means and a second step for causing the tracking means to start the tracking with the amplification gain determined by the first step.

Figure 5:
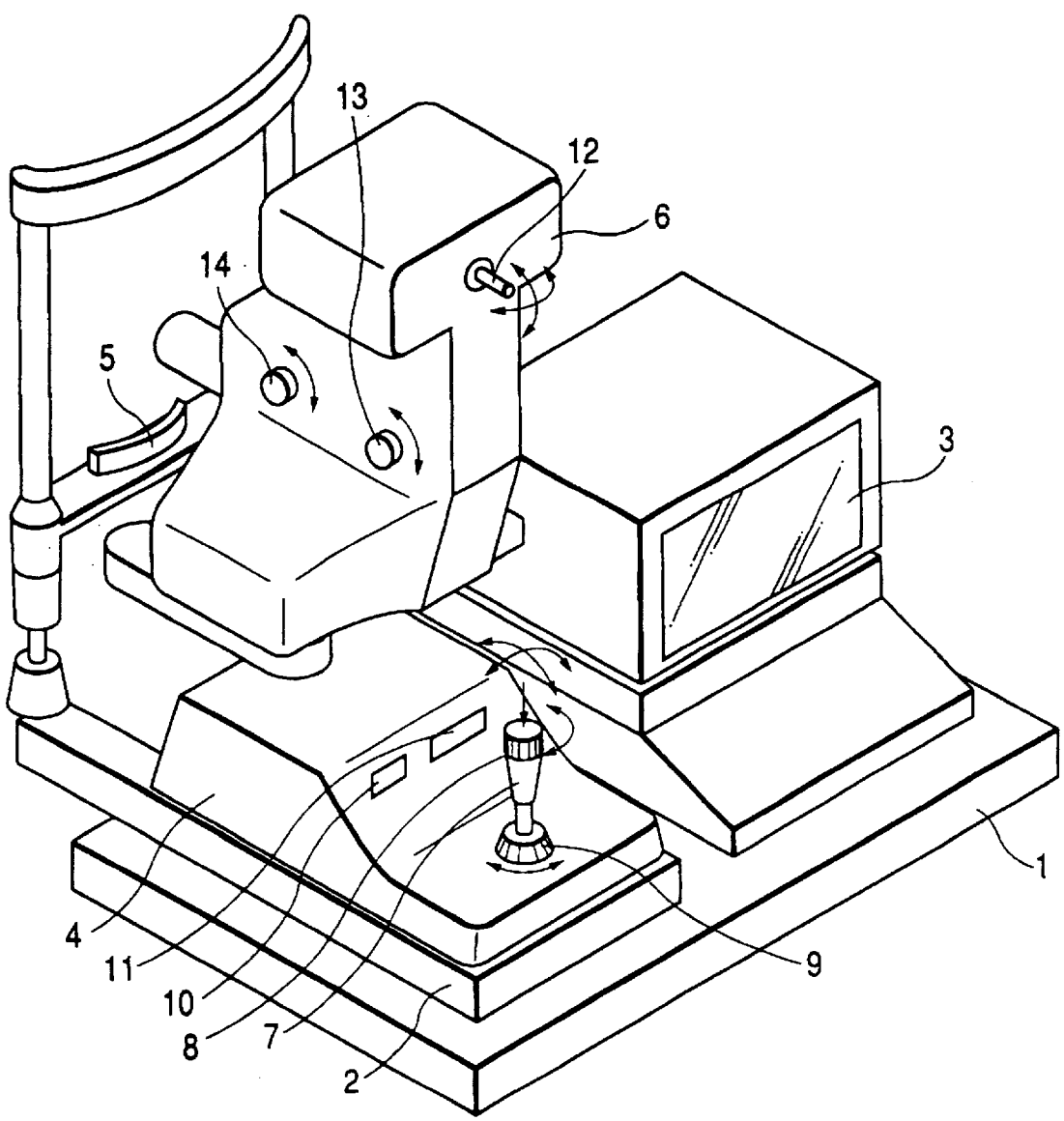
FIG. 5 is a perspective view of an embodiment of the present invention.

FIG. 5 is a perspective view of the eye fundus blood flow meter of the present embodiment, wherein a base member 1 supports a monitor 3 and a fixed stage unit 2, which in turn, supports a movable stage unit 4 rendered movable in the forward-backward direction and in the lateral direction, and a chin support member 5. On the movable stage unit 4 there is provided a measuring head 6, and, at the examiner side of the movable stage 4 there are provided an operating rod 7, a switch 8, an operation ring 9, a measuring mode selecting switch 10 and an LED 11 for display. Also on the measuring head 6 there are provided an operation knob 12 for moving a fixation target, a focusing knob 13, and an image rotator knob 14.

Figure 6:
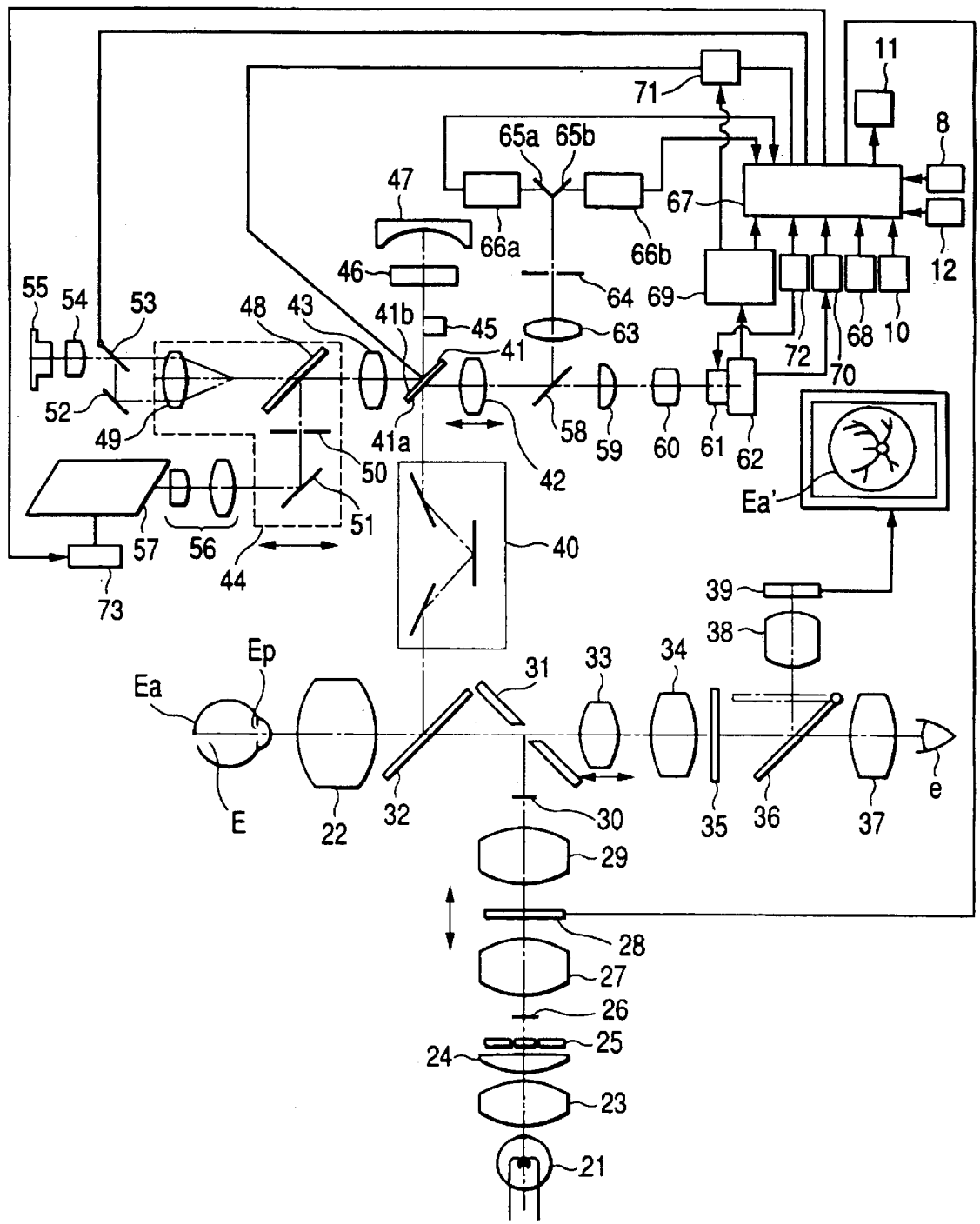
FIG. 6 is a view showing the configuration of a measuring head of the present invention.

FIG. 6 is a view showing the configuration of a main body of the eye fundus blood flow meter, incorporated in the measuring head 6, wherein, on an illumination optical path from an observation light source 21 composed for example of a tungsten lamp emitting white light to an objective lens 22 provided in a position opposed to the eye to be examined E, there are in succession provided a condenser lens 23, a field lens 24 with a band-pass filter for transmitting, for example, the light of the yellow wavelength region only, a ring slit 25 substantially conjugate with the pupil Ep of the eye to be examined E, a light shield member 26 substantially conjugate with the lens of the eye to be examined E, a relay lens 27, a transmissive liquid crystal panel 28 rendered movable along the optical path and constituting a fixation target displaying element, a relay lens 29, a light shield member 30 conjugate with the vicinity of the cornea of the eye to be examined E, a holed mirror 31, and a band-pass mirror 32 transmitting light of the yellow wavelength region and substantially reflecting light of other wavelength regions, thereby constituting an illumination optical system.

The ring slit 25 and the light shield members 26, 30 serve to separate the eye fundus illuminating light and the eye fundus observing light at the front eye region of the eye to be examined E, and the shape of these components is not critical as a long as suitable light shielding area can be formed.

Behind the holed mirror 31 there is provided an eye fundus observing optical system, which is provided, in succession on the path to the observing eye e, a focusing lens 33 movable along the optical path, a relay lens 34, a scale plate 35, an optical path switching mirror 35 insertable into and retractable from the optical path, and an eyepiece lens 37. In an optical path in the direction of reflection of the optical path switching mirror 37 when it is inserted into the optical path, there are provided a television relay lens 38 and a CCD camera 39 whose output is supplied to a CRT monitor 3.

Also in an optical path in the direction of reflection of the band-pass filter 32, there are provided an image rotator 40 and a galvanometric mirror 41 polished on both faces and having a rotary axis perpendicular to the plane of the drawing, and in the direction of reflection of the lower reflective face 41a of the galvanometric mirror 41 provided is a second focusing lens 42 movable along the optical path, while, in the direction of reflection of the upper reflective face 41b, there are provided a lens 43 and a focusing unit 44. The front focal plane of the lens 43 is conjugate with the pupil Ep of the eye to be examined E and the galvanometric mirror 41 is positioned on such focal plane.

Above the galvanometric mirror 41 there are provided an optical path length compensating semicircular plate 45, a black spot plate 46 having a light shield portion in the optical path, and a concave mirror 47 positioned in a concentric manner on the optical axis, thereby constituting a relay optical system for guiding the light beam, which is not reflected by the lower reflective face 41a of the galvanometric mirror 41, to the upper reflective face 41b thereof. The optical path length compensating semicircular plate 45 is designed to compensate for the aberration, in the vertical direction of the drawing, resulting from the thickness of the galvanometric mirror between the upper reflective face 41b and the lower reflective face 41a thereof, and functions only in the optical path toward the image rotator 40.

In the focusing unit 44 there are provided, on the optical path of the lens 43, a dichroic mirror 48 and a condenser lens 49, and, on an optical path in the direction of reflection of the dichroic mirror 48, there are provided a mask 50 and a mirror 51. The focusing unit 44 is rendered integrally movable in a direction indicated by an arrow, along the optical path.

On an optical path at the entrance side of the condenser lens 49, there are provided in a parallel manner a fixed mirror 52 and an optical path switching mirror 53 retractable from the optical path, and, on an optical path at the entrance side of the optical path switching mirror 53, there are provided a collimating lens 54 and a measuring laser diode 55 emitting coherent light, such as light of a red color. Furthermore, on an optical path at the entrance side of the mirror 51 there are provided a beam expander 56 composed, for example, of a cylindrical lens, and a tracking light source 57 emitting light of a high intensity of a color, for example green, different from that of the other light source.

On an optical path behind the second focusing lens 42, there are in succession provided a dichroic mirror 58, a field lens 59, a magnifying lens 60 and a one-dimensional CCD 62 with an image intensifier, thereby constituting a vessel detection system. Also on an optical path in the direction of reflection by the dichroic mirror 58, there are provided an imaging lens 63, a confocal diaphragm 64 and paired mirrors 65a, 65b substantially conjugate with the pupil Ep of the eye to be examined E, and, in the directions of reflection by the paired mirrors 65a, 65b there are respectively provided photomultipliers 66a, 66b to constitute measuring light receiving optical systems. All the optical paths are, illustrated on a same plane for the purpose of simplicity, but the optical path from the laser diode 55 to the mask 50, the measuring optical path at the exit side of the tracking light source 57 and the reflection optical paths of the paired mirrors 65a, 65b are in fact perpendicular to the plane of the drawing.

For controlling the entire apparatus there is provided a system control unit 67, to which is supplied the outputs of the switch 8, the measuring mode selection switch 10, the operation knob 12, the photomultipliers 66a, 66b and lateral movement detection means 68. The output of the one-dimensional CCD 62 is supplied through a vessel detection circuit 69 and an A/D converter 70 to the system control unit 67, while the output of the vessel detection circuit 69 is supplied to the system control unit 67 and to a galvanometric mirror control circuit 71 for controlling the galvanometric mirror 41, and the output of the system control unit 67 is supplied, through the display LED 11, the transmissive liquid crystal panel 28, the optical path switching mirror 53, the galvanometric mirror control circuit 71 and a D/A converter 72, to a driving power source 73 for the tracking light source 57 and the image intensifier 61.

Figure 7:
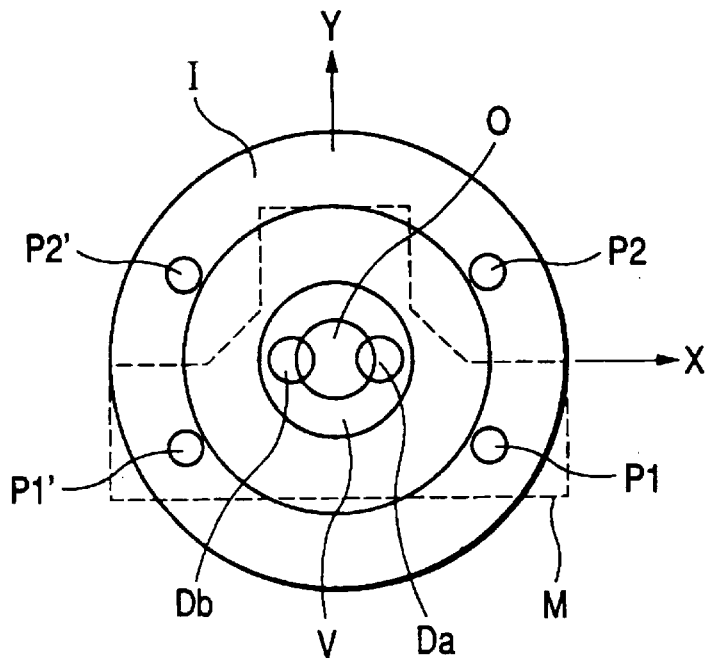
FIG. 7 is a view showing the arrangement of light beams on the pupil, in the present invention.

FIG. 7 shows the arrangement of light beams on the pupil Ep of the eye to be examined E, wherein I indicates an area illuminated with the yellow illuminating light and shows an image of the ring slit 25, O indicates an eye fundus observing light beam and shows an image of the aperture of the holed mirror 31, V indicates a measuring light beam/beam received from the vessel and shows an image of effective portions of the upper and lower reflective faces 41b, 41a of the galvanometric mirror 41, and Da, Db indicate two received measuring beams and respectively show images of the paired mirrors 65a, 65b. Also P1, P1' indicate the entering positions of the measuring light, selected by the switching of the optical path switching mirror 53, and a chain-lined area M indicates an image of the lower reflective face 41a of the galvanometric mirror 41.

At the measurement, the examiner at first fixes the face of the examinee on the chin support member 5, and selects, for example, a mode for measuring a vessel in the vicinity of the disc by the measuring mode selecting switch 10. The lateral position of the movable stage 3 is detected by the lateral movement detection means 68 to discriminate whether the eye to be examined is the left or right eye, and the signals from the lateral movement detection means 68 and the measuring mode selecting switch 10 are supplied to the system control unit 67. In response to these signals, a predetermined dot pattern Q is displayed as the fixation target on the transmissive liquid crystal panel 38, and the observation light source 21 is turned on.

The white light emitted from the observing light source 21 is transmitted by the condenser lens 23. Then, the light of the yellow wavelength region only is transmitted by the field lens 24 with the band-pass filter, is further transmitted by the ring slit 25, the light shield member 26 and the relay lens 27, illuminates the transmissive liquid crystal plate 28 from the rear side, is further transmitted by the relay lens 29 and the light shield member 30, and is reflected by the holed mirror 31. Thus, the light of the yellow wavelength region only is transmitted by the band-pass mirror 32 and the objective lens 22 and is focused as an image I of the eye fundus illuminating light beam on the pupil Ep of the eye to be examined E, thus substantially uniformly illuminating the eye fundus Ea.

In this state, the transmissive liquid crystal plate 28 displays one of the dot patterns Q, which is projected by the illuminating light onto the eye fundus Ea of the eye to be examined E and is presented thereto as an fixation target image F. The examiner manipulates the operating knob 12 to send a signal to the system control unit 67, thereby varying the position of the displayed dot pattern Q and guiding the visual axis of the eye to be examined E.

The light reflected by the eye fundus Ea returns on the same optical path and is taken out, from the pupil Ep, as an eye fundus observing light beam O, which is guided through the central hole of the holed mirror 31, the focusing lens 33, and the relay lens 34, is then focused as an eye fundus image Ea' by the scale plate 35 and reaches the optical path switching mirror 36. When the optical path switching mirror 36 is retracted from the optical path, the observing eye e can observe the eye fundus image Ea' through the eyepiece lens 37, but, when the optical path switching mirror 36 is inserted into the optical path, the eye fundus image Ea' focused on the scale plate 35 is refocused on the CCD camera 39 through the television relay lens 38 and is displayed on the monitor 3.

The alignment of the apparatus with the eye to be examined E is made by the manipulation of the operating rod 7 and the operating ring 9 to move the movable stage 4 in the X-Z plane and in the Y-direction, under the observation of the eye fundus image Ea' either through the eyepiece lens 37 or the monitor 3. In this operation it is desirable to select the appropriate observing method according to the desired purpose. The observation through the eyepiece lens 37, being generally higher in resolving power and in sensitivity than the observation by the monitor 3, is suitable for diagnosis by reading delicate changes on the eye fundus Ea. On other hand, the observation through the monitor 3 is also very useful for clinical purposes since such observation, not limited in the viewing field, can reduce the fatigue of the examiner and allows electronic recording of the successive changes in the measured region of the eye fundus image Ea' by supplying the output of the CCD camera 39 to an external video cassette recorder or an external video printer.

Then, the measuring laser diode 55 and the tracking light source 57 are turned on. The measuring light, emitted from the laser diode 55, is collimated by the collimating lens 54 and, if the optical path switching mirror 53 is inserted in the optical path, is reflected by this mirror 53 and the fixed mirror 52 to pass through the lower part of condenser lens 49, but, if the optical path switching mirror 53 is retracted from the optical path, it directly passes through the upper part of condenser lens 49, thus being transmitted by the dichroic mirror 48.

On the other hand, the tracking light emitted from the tracking light source 57 is expanded in beam diameter with different magnifications in the vertical and horizontal directions by the beam expander 56, then is reflected by the mirror 51, is shaped into a desired shape by the shaping mask 50, is further reflected by the dichroic mirror 48 and is superposed by the condenser lens 49 with the measuring light which is focused into a spot at a position conjugate with the center of the aperture of the mask 50.

The measuring light, which are and the tracking light mutually superposed, are transmitted by the lens 43, reflected by the upper reflective face 41b of the galvanometric mirror 41, transmitted by the black spot plate 46, reflected by the concave mirror 47, again transmitted by the black spot plate 46 and the optical path length correcting semicircular plate 45, and are returned toward the galvanometric mirror 41.

By the function of the relay optical system, which consists of the concave mirror 47, the black spot plate 46 and the optical path length compensating semicircular plate 45, and which forms the images of the upper reflective face 41b and the lower reflective face 41a of the galvanometric mirror 41 with a magnification of −1, the measuring light and the tracking light reflected at positions P1, P1' shown in FIG. 3, behind the image M of the galvanometric mirror 41, are returned, by the insertion or retraction of the optical path switching mirror 53 into or from the optical path, to positions P2, P2' corresponding to a notched portion of the galvanometric mirror 41, so that these lights are guided to the image rotator 40 without being reflected by the galvanometric mirror 41. Then, the both light beams are deflected by the band-pass filter 32 toward the objective lens 22 and are projected therethrough to the eye fundus Ea of the eye to be examined E.

In this manner the measuring light and the tracking light are reflected by the upper reflective face 41b of the galvanometric mirror 41, and, in the returning state, they enter the galvanometric mirror 41 in a state deviated from the optical axis of the objective lens 22, whereby, on the pupil Ep, the light beam passing through the positions P1 and P2 forms a spot image P, while the light beam passing through the positions P1' and P2' forms a spot image P', thereby illuminating the eye fundus Ea in spot shapes.

The light scattered and reflected at the eye fundus Ea is condensed by the objective lens 22, is then reflected by the band-pass filter 32, transmitted by the image rotator 40, and reflected by the lower reflective face 41a of the galvanometric mirror 41, and the measuring light and the tracking light are separated by the dichroic mirror 58.

The tracking light is transmitted by the dichroic mirror 58, and is focused by the field lens 59 and the imaging lens 60 on the one-dimensional CCD 62 through the image intensifier 61 as a vessel image Ev', which is magnified to a greater extent than the eye fundus image Ea' formed by the eye fundus observing optical system. On the other hand, the measuring light is reflected by the dichroic mirror 58, is then transmitted by the aperture of the confocal diaphragm 64, reflected into two directions by the paired mirrors 65a, 65b and received by the photomultipliers 66a, 66b.

In this state, because of the spectral characteristics of the band-pass mirror 32, the illuminating light from the observing light source 21 does not reach the one-dimensional CCD 62, and undesirable flare is reduced because a narrow image taking area is selected. As a result, the one-dimensional CCD 62 only takes the vessel image Ev' formed by the tracking light. Also, since hemoglobin in the blood and melamine in the pigment epithelium are significantly different in spectral reflectance in the green wavelength region, the vessel image Ev' can be obtained with a satisfactory contrast by employing green tracking light.

The light beam received by the one-dimensional CCD 62 is taken out from the measuring/vessel-received light beam V from the vessel at the pupil Ep of the eye to be examined E, and measuring/received light beams Da, Db are taken out therefrom by the paired mirrors 65a, 65b and are received by the photomultipliers 66a, 66b. The measuring/vessel-received light beam V is made larger than the eye fundus observing light beam O because otherwise, a sufficient image plane intensity on the one-dimensional CCD 62 cannot be obtained as the one-dimensional CCD 62 has a larger imaging magnification for the eye fundus Ea than in the CCD camera 39 of the eye fundus observing optical system. On the other hand, the influence of flare, generated at the front eye region of the eye to be examined E by the enlargement of the light beam is negligible because the image receiving area is smaller in the vessel image receiving optical system. Also, the distance of the received measuring light beams Da, Db on the pupil E, directly affecting the resolving power of the blood flow velocity measurement, can be made sufficiently large by employing a large measuring/received light beam V.

Figure 8:
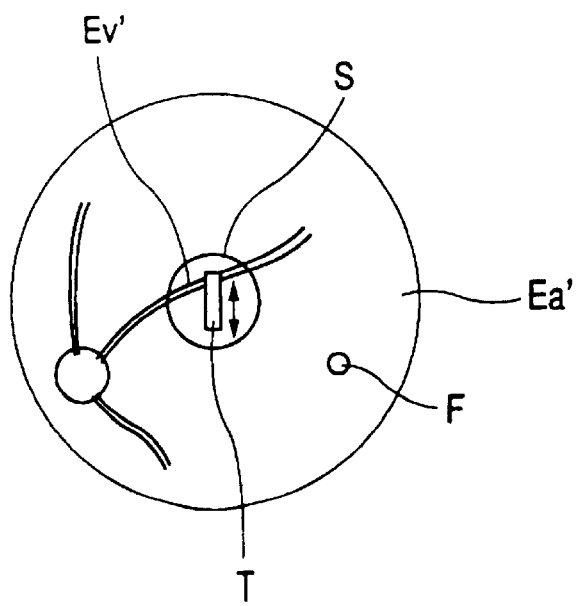
FIG. 8 is a schematic view showing an eye fundus image in the present invention.

A part of the measuring and tracking lights scattered and reflected on the eye fundus Ea is transmitted by the band-pass mirror 32 and guided to the eye fundus observing optical system positioned behind the holed mirror 31, wherein the tracking light is focused on the scale plate 35 as a rod-shaped indicator T, while the measuring light is focused as a spot at the center of the indicator T. FIG. 8 shows the eye fundus image Ea' observed through the eyepiece lens 37 or the monitor 3, including a vessel image Ev', an image F of the fixation target projected by the illuminating light onto the eye fundus, an indicator T superposed with an unrepresented spot image, and a circular scale S formed on the scale plate 35 and projected onto the eye fundus Ea. Under the observation of an such image, the examiner can one-dimensionally move the indicator T within a range that the center of the indicator T is contained in the scale S, by the rotation of the switch 8.

When the examiner rotates the focusing knob 13 for focusing the eye fundus image Ea', the transmissive liquid crystal panel 28, the focusing lenses 33, 42 and the focusing unit 44 are moved in mutual linkage, by unrepresented drive means, along the optical axis. When the eye fundus image Ea' is focused, all the transmissive liquid crystal panel 28, the scale plate 35, the one-dimensional CCD 62, and the confocal diaphragm 64 become conjugate with the eye fundus Ea.

After the focusing operation, the examiner manipulates the operating knob 12, if necessary, to move the fixation target F, thereby guiding the visual axis of the eye to be examined E, thus varying the observed area and moving the target vessel Ev into the circle S of the scale plate 35. Then, the examiner drives the image rotator 40 by the image rotator knob 14, thereby rotating the indicator T in such a manner that it becomes perpendicular to the longitudinal direction of the target vessel Ev.

In this operation, the examiner recognizes whether the indicator alone rotates, since the eye fundus observing light does not pass through the image rotator 40. Consequently, also the images of the optical components on the pupil Ep as shown in FIG. 7 rotate in the same direction and by the same angle about the original point, so that a line passing through the centers of the measuring/received light beams Da, Db and the X-axis passing through the centers of the spot images P, P' become parallel to the longitudinal direction of the vessel Ev. As the blood flow velocity is determined from the interference between the scattered/reflected light from the vessel wall and that from the blood cells in the blood, the result of measurement is not influenced by the movement of the eye fundus Ea in the X-direction in the course of measurement, if the vessel Ea is positioned substantially parallel to the X-axis.

On the other hand, in case the eye fundus Ea moves in a direction of the Y-axis, which is perpendicular to the X-axis, the result of measurement becomes unstable because the light beam from the measuring laser diode 55 becomes deviated from the target vessel Ev, but, in such case, the amount of displacement of the vessel Ev need only be detected in the Y-direction. In the present embodiment, the tracking operation is executed only in such direction by the vessel detecting system behind the dichroic mirror 58 and by the galvanometric mirror 41.

Figure 9:
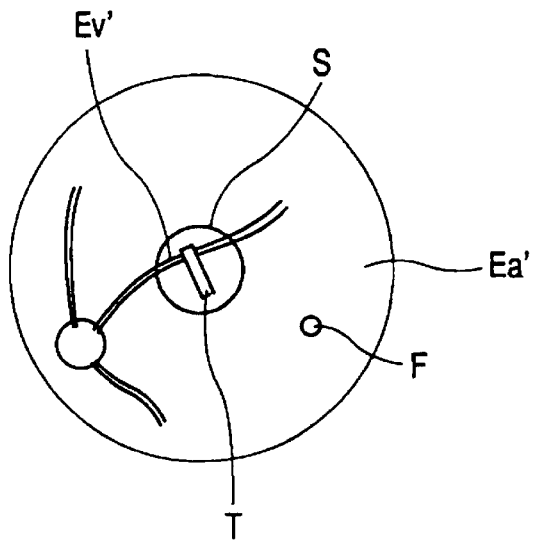
FIG. 9 is a schematic view showing a rotation of an indicator according to the present invention.
Figure 10:
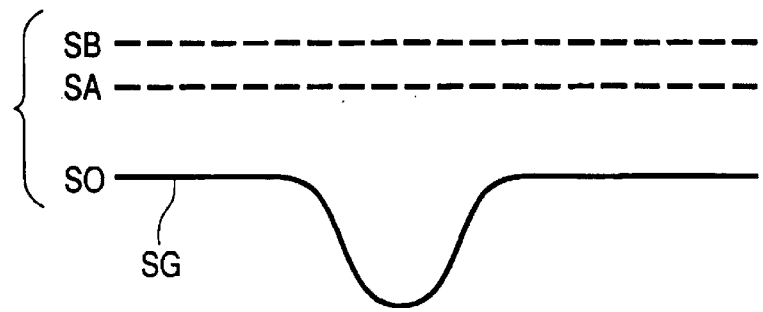
FIG. 10 is a chart showing the signal of the one-dimensional CCD prior to the gain control, in the present invention.

As the elements of the one-dimensional CCD 62 are arranged in the longitudinal direction of the tracking light, in a state where the angular adjustment of the inspected region is completed as shown in FIG. 9, the longitudinal direction of the indicator T, indicating the tracking light, is perpendicular to the longitudinal direction of the inspected vessel Ev, whereby the one-dimensional CCD 62 of the vessel detecting system takes the eye fundus image Ea indicated by the indicator T in a magnified manner. As the green tracking light is absorbed by the blood vessel, the output signal SG of the one-dimensional CCD 62 shows a recess, as shown in FIG. 10, at the crossing portion of the indicator T and the vessel Ev.

Figure 11:
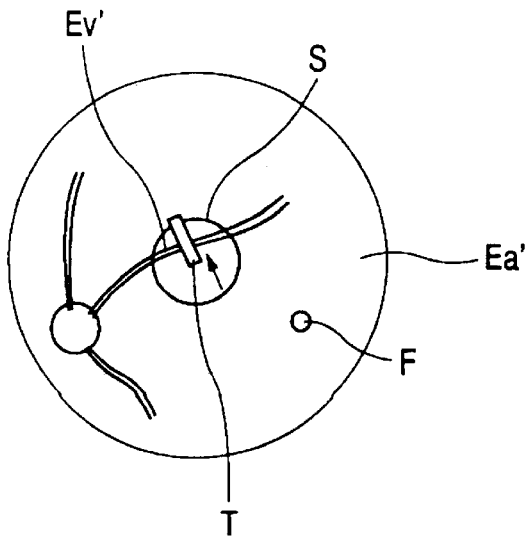
FIG. 11 is a schematic view showing a movement of the indicator in the present invention.

After the angular adjustment, the switch 8 is again rotated to move the indicator T as indicated by an arrow in FIG. 11, and the region to be measured is selected by matching the light spot, superposed with the tracking light, with such region. After the determination of the region to be measured, the switch 8 is pressed in to send a signal for starting the tracking operation after the positioning operation.

Figure 12:
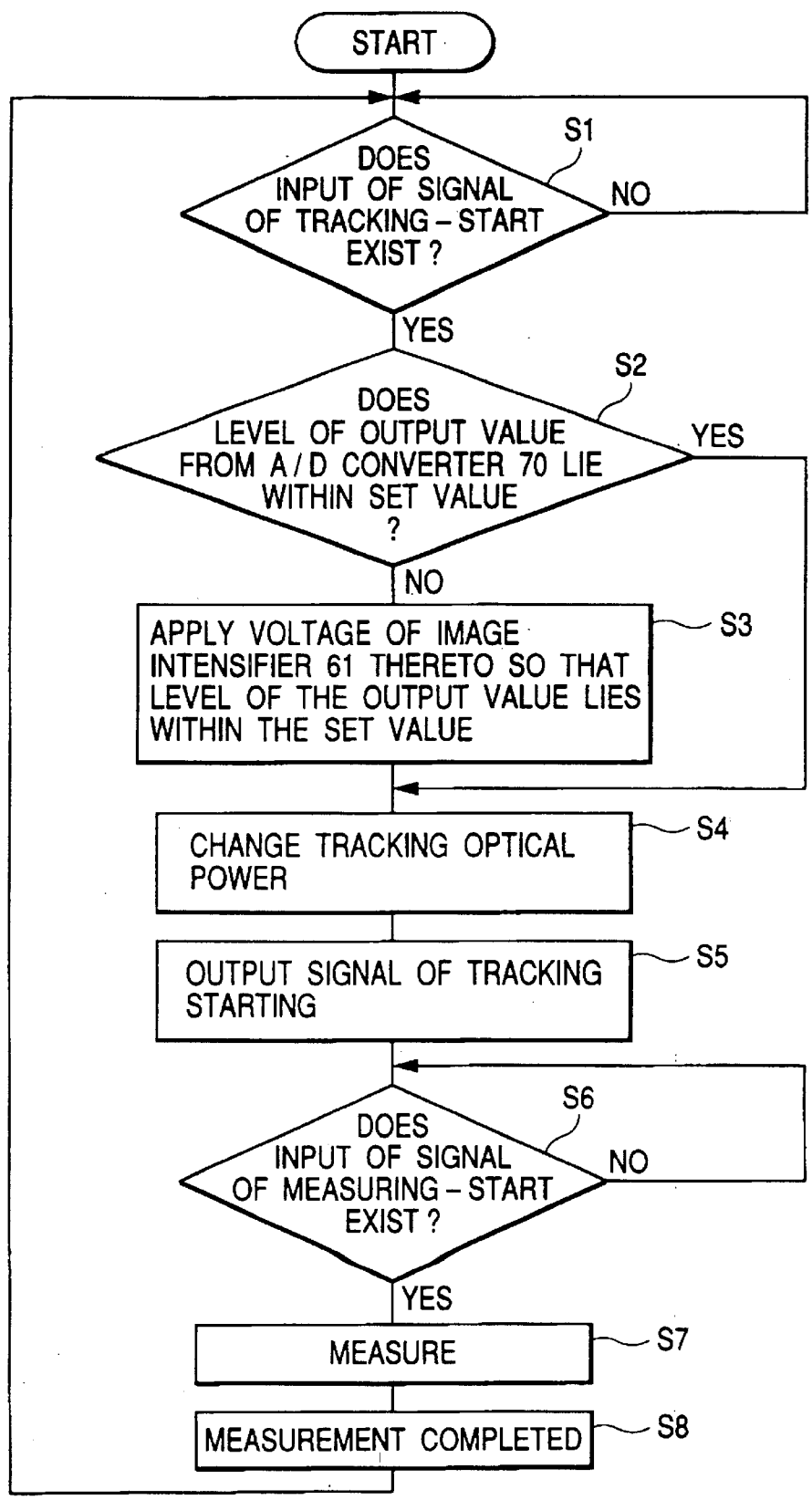
FIG. 12 is a flow chart showing the control sequence of the system control unit of the present invention.

In response to the tracking start signal entered from the switch 8, the system control unit 67 functions according to the flow chart shown in FIG. 12. A step S1 discriminates whether a tracking start signal has been entered from the switch 8, and, if entered, a step S2 executes A/D conversion of the signal SG from the one-dimensional CCD 62, shown in FIG. 10, by the A/D converter 70. Then, there is discriminated whether the signal SG is positioned within a range between values SA and SB which are shown in FIG. 10 and are present with such an initial power that is anticipated to bring the signal SG, coming from an area outside the vessel, to a preferred level in case the power of the tracking light irradiating the eye to be examined E is increased. If the signal SG is not within such range, a step S3 determines the voltage to be applied to the image intensifier 61 in such a manner that the signal SG falls between the set values SA and SB, and sends necessary data to the D/A converter 72 to execute such voltage application. In the present embodiment, the signal level of the vessel image Ev' is optimized by the control of the voltage applied to the image intensifier, but there may be controlled the gain of the amplifier of the one-dimensional CCD 62 for the same purpose.

Figure 13:
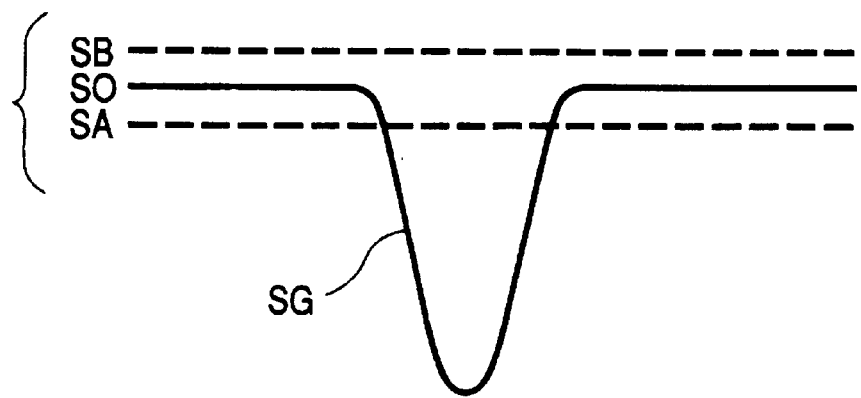
FIG. 13 is a chart showing the signal of the one-dimensional CCD after to the gain control, :in the present invention.

If the signal SG from an area outside the vessel is positioned between the set values SA and SB as shown in FIG. 13 from the beginning or after the step S3, the voltage applied to the image intensifier 61 is fixed, and, in a step S4, the system control unit 67 supplies the driving power source 73 with an instruction to increase the power of the tracking light to a preset power level required for ensuring the tracking operation.

Then, in a step S5, the system control unit 67 supplies the galvanometric mirror control circuit 71 with a tracking start signal, and the vessel detection circuit 71 calculates, based on the output signal of the one-dimensional CCD 62, the amount of displacement of the vessel image Ev' from a one-dimensional reference position. Based on such amount of displacement, the galvanometric mirror control circuit 71 drives the galvanometric mirror 41 in such a manner that the position of the vessel image Ev' remains constant on the one-dimensional CCD 62.

After confirming the start of tracking, the examiner presses in the switch 8 further to initiate the measurement by a second-stroke switch. The system control unit 67 awaits, in a step S6 of the flow chart in FIG. 12, the entry of the measurement start signal from the switch 8, and, in response to the entry of the signal, a step S7 executes the measurement of the blood flow velocity. Then, a step S8 terminates the measurement and the sequence returns to the step S1.

In the measurement, the system control unit 67 at first inserts the optical path switching mirror 53 into the optical path, whereby the light beam entering from the spot image P on the pupil Ep of the eye to be examined E is received by the photomultipliers 66a, 66b, and the output signals thereof are fetched and processed in the system control unit 67 to obtain maximum frequency shifts |Δfmax1| and |Δfmax2|.

Since the incident light in this state comes from the spot image P which is sufficiently displaced from the received measuring light beams Da, Db, the maximum velocity is normally given by the following equation (1):

$$Vmax = \{(\lambda/(n \cdot \alpha)\} \cdot ||\Delta fmax1| - |\Delta fmax2|| \tag{1}$$

wherein λ is the wavelength of the measuring light beam, n is the refractive index of the measured region, and a is the angle formed by the measuring light beam and the received light beam.

However, depending on the position of the vessel Ev on the eye fundus Ea, the true maximum velocity Vmax may have to be determined by the following equation (2):

$$Vmax = \{(\lambda/(n \cdot \alpha)\} \cdot ||\Delta fmax1| + |\Delta fmax2|| \tag{2}$$

After a temporary measurement is executed in this state and the maximum velocity Vmax is calculated by the equation (1), the optical path switching mirror 53 is retracted from the optical path by the system control unit 67, and the measurement is executed again by introducing the light beam from the spot image P' on the pupil Ep of the eye to be examined E.

The center of the spot image P' is so positioned on the pupil Ep, as shown in FIG. 7, as to be on a line passing through the center of the other spot image P and parallel to the line connecting the centers of the received measuring light beams Da, Db. In the present embodiment, in particular, the spot image P' is so selected that the distance between the spot images P and P' is larger than the distance between the centers of the received measuring light beams Da, Db and that a line connecting the middle points of the above-mentioned two lines is perpendicular to these two lines.

After the incident light is switched from the spot image P to the thus selected spot image P', the system control unit 67 again fetches the signals from the two photomultipliers 66a, 66b to calculate the respective maximum frequency shifts |Δfmax1'| and |Δfmax2'|, and obtains the maximum velocity Vmax according to the equation (1). Through the comparison of the two maximum velocities Vmax and Vmax', the system control unit 67 determines an appropriate incident direction of the light beam for obtaining the true maximum velocity, then executes appropriate optical path switching based on the thus obtained information, and continues the measurement by repeating the calculation of the maximum velocity Vmax or Vmax' at a suitable interval. The maximum blood flow velocity Vmax or Vmax' obtained in this manner is displayed on the LED 11, and the measurement of the vessel Ev to the right of the disc is thus completed.

In the present embodiment there has been explained a tracking operation by selecting a part of a vessel Ev, but it is also possible to select the target region of tracking from each of plural vessels Ev or a characteristic region other than the vessel, such as a disc as the target region of tracking. Furthermore, the tracking may be executed, instead of selecting a characteristic region as the target, by selecting a broad area of the eye fundus Ea as the target.

As explained in the foregoing, the ophthalmic apparatus of the present invention automatically and promptly controls the gain of the detection means after the preparation for the tracking operation to the selected position but prior to the execution of tracking, thereby enabling measurement with the minimum light irradiation to the examinee without the cumbersome gain adjusting operation and without requiring a long time. Also, in case the power of the tracking light is changed between before and during the tracking operation in order to reduce the energy of the tracking light given to the examinee, the gain of the detection means can be controlled in consideration of such change.

In the following there will be explained an apparatus comprising illumination means for illuminating an area including a specified target region of the eye fundus; image taking means for taking the image of the specified region, thereby outputting an image signal; process condition determination means for determining the process condition, based on the output signal from the image taking means or a signal in the vicinity of the specified region contained in the result of processing of such an output signal; region extracting means for extracting the specified region according to the process condition determination means; and auto tracking means for automatically tracking the specified region based on the output of the region extracting means.

Also, a next embodiment provides an ophthalmic inspecting apparatus comprising illumination means for illuminating an area including a specified target region of the eye fundus; image taking means for taking the image of the specified region, thereby outputting an image signal; process condition determination means for determining the process condition, based on the output signal from the image taking means or a signal in the vicinity of the specified region contained in the result of processing of such an output signal; region extracting means for extracting the specified region according to the process condition determination means; and auto tracking means for automatically tracking the specified region based on the output of the region extracting means.

Figure 14:
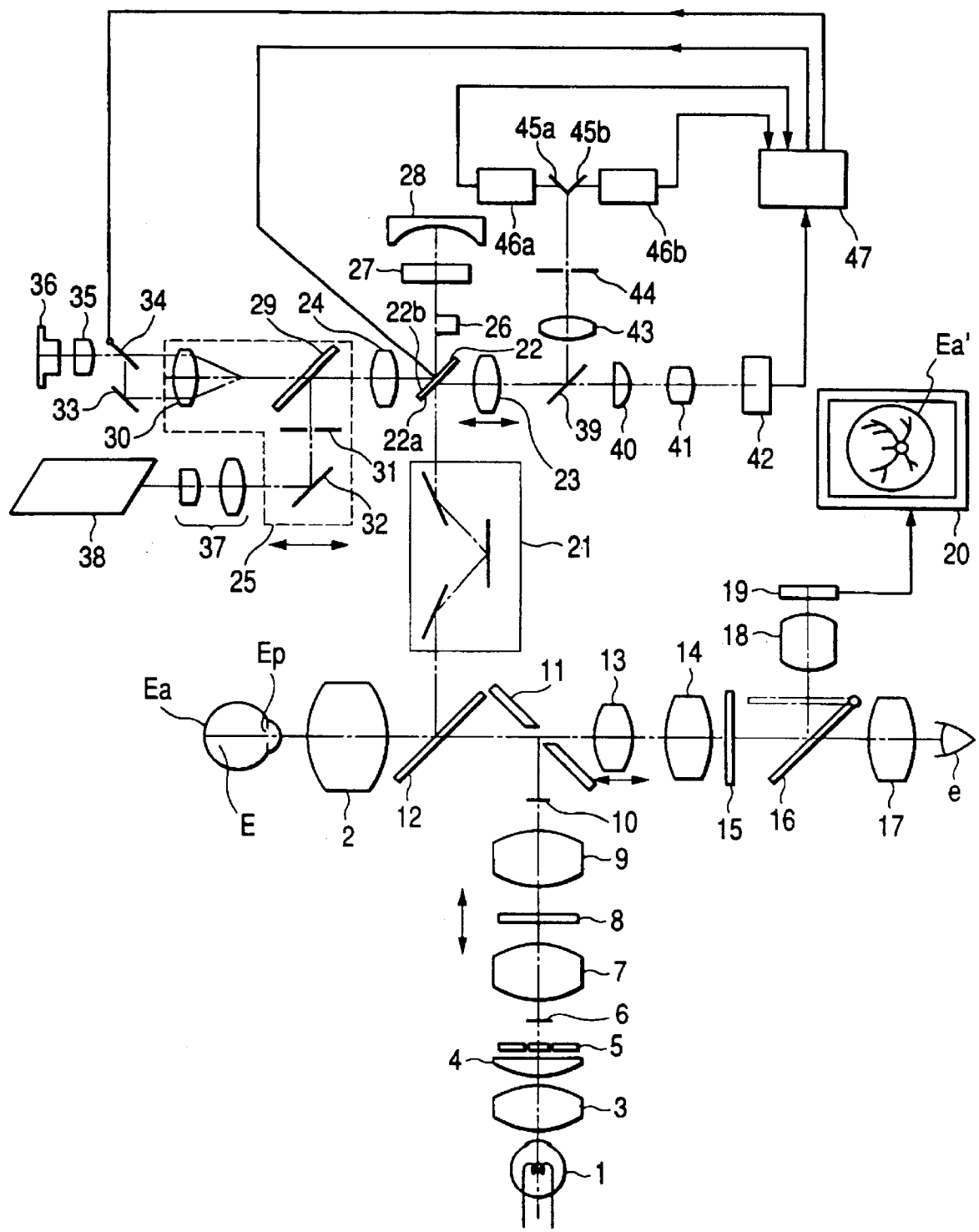
FIG. 14 is a view showing the configuration of another embodiment.

FIG. 14 shows the configuration of an eye fundus blood flow meter constituting an embodiment of the present invention, in which, on an illumination light path from an observation light source 1, composed, for example, of a tungsten lamp emitting white light, to an objective lens 2 opposed to an eye to be examined E, there are, in succession, provided a condenser lens 3, a field lens 4 with a band-pass filter transmitting; for example, only the yellow wavelength region, a ring slit 5 substantially conjugate with the pupil Ep of the eye to be examined E, a light shield member 6 substantially conjugate with the lens of the eye to be examined E, a relay lens 7, a transmissive liquid crystal panel 8 rendered movable along the optical path and serving as a fixation target display element, a relay lens 9, a light shield member 10 conjugate with the vicinity of the cornea of the eye to be examined E, a holed mirror 11, and a band-pass filter 12 transmitting light of the yellow wavelength region and reflecting the light of most of other wavelength regions.

Behind the holed mirror 11 there is provided an eye fundus observing optical system, which is provided, in succession in the path to the observing eye e, a focusing lens 13 movable along the optical path, a relay lens 14, a scale plate 15, an optical path switching mirror 15 insertable into and retractable from the optical path, and an eyepiece lens 17. In an optical path in the direction of reflection of the optical path switching mirror 16 when it is inserted into the optical path, there are provided a television relay lens 18 and a CCD camera 19 whose output is supplied to a liquid crystal monitor 20.

Also, in an optical path in the direction of reflection of the band-pass filter 12, there are provided an image rotator 21 and a galvanometric mirror 22 polished on both faces and having a rotary axis perpendicular to the plane of drawing, and in the direction of reflection of the lower reflective face 22a of the galvanometric mirror 22 provided is a second focus lens 23 movable along the optical path, while, in the direction of reflection of the upper reflective face 22b, there are provided a lens 24 and a focusing unit 25 movable along the optical axis. The front focal plane of the lens 24 is conjugate with the pupil Ep of the eye to be examined E and the galvanometric mirror 22 is positioned on such a focal plane.

Behind the galvanometric mirror 22 there are provided an optical path length compensating semicircular plate 26, a black spot plate 27 having a light shield region in the optical path, and a concave mirror 28 positioned in concentric manner on the optical axis, thereby constituting a relay optical system for guiding the light beam, which is not reflected by the lower reflective face 22a of the galvanometric mirror 22, to the upper reflective face 22b thereof. The optical path length compensating semicircular plate 25 is designed to compensate for the aberration, in the vertical direction of the drawing, resulting from the thickness of the galvanometric mirror 22 between the upper reflective face 22b and the lower reflective face 22a thereof, and functions only in the optical path toward the image rotator 21.

In the focusing unit 25 there are provided, on the optical path of the lens 24, a dichroic mirror 29 and a condenser lens 30, and, on an optical path in the direction of reflection of the dichroic mirror 29 there are provided a shaping mask 31 and a mirror 32. The focusing unit 25 is rendered integrally movable in a direction indicted by an arrow, along the optical path.

On an optical path at the entrance side of the condenser lens 30, there are provided in a parallel manner a fixed mirror 33 and an optical path switching mirror 34 retractable from the optical path, and, on an optical path at the entrance side of the optical path switching mirror 34, there are provided a collimating lens 35 and a measuring laser diode 36 emitting coherent light, such as light of a red color. Furthermore, on an optical path at the entrance side of the mirror 32 there are provided a beam expander 37 composed, for example, of a cylindrical lens, and a tracking light source 38 emitting light of a high intensity of a color, for example green, different from that of the other light source.

On an optical path behind the second focusing lens 23, there are in succession provided a dichroic mirror 39, a field lens 40, a magnifying lens 41 and a one-dimensional CCD 42 with an image intensifier, thereby constituting a vessel detection system. Also, on an optical path in the direction of reflection by the dichroic mirror 39, there are provided an imaging lens 43, a confocal diaphragm 44 and paired mirrors 45a, 45b substantially conjugate with the pupil Ep of the eye to be examined E, and, in the directions of reflection by the paired mirrors 45a, 45b, there are respectively provided photomultipliers 46a, 46b to constitute measuring light receiving optical systems.

All the optical paths are illustrated on a same plane for the purpose of simplicity, but the optical path from the laser diode 36 to the mask 31, the measuring optical path at the exit side of the tracking light source 38 and the reflection optical paths of the paired mirrors 45a, 45b are in fact perpendicular to the plane of the drawing.

For controlling the entire apparatus there is provided a system control unit 47, to which are supplied the outputs of the one-dimensional CCD 42 and of the photomultipliers 46a, 46b, and the output of the system control unit 47 is supplied to the galvanometric mirror 22 and the optical path switching mirror 34.

Figure 15:
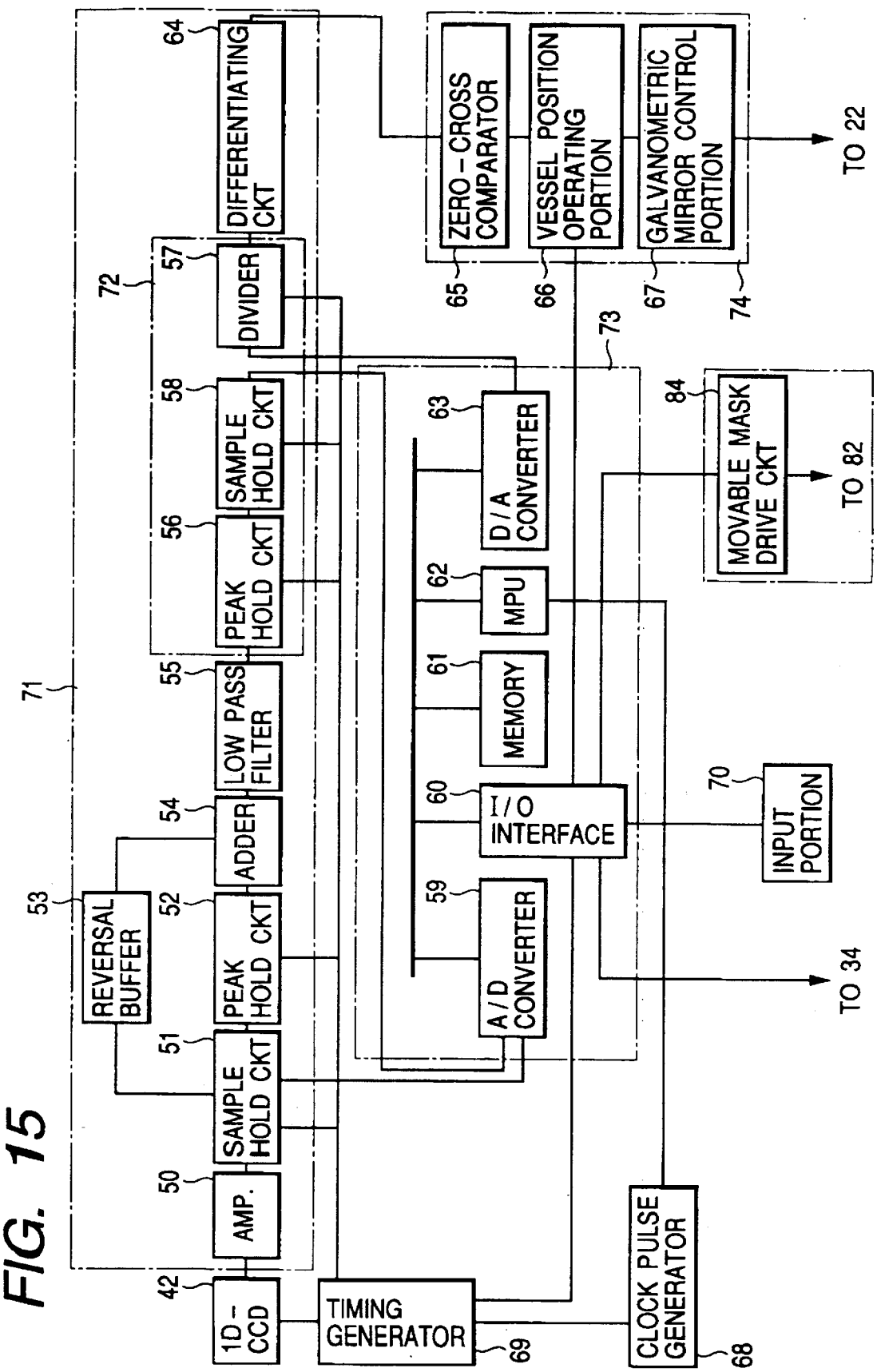
FIG. 15 is a view showing the configuration of a block circuit in the system control unit.

FIG. 15 shows the configuration of the system control unit 47, in which the output of the one-dimensional CCD 42 is connected in succession to an amplifier 50 and a sample hold circuit 51, whose output is connected to a peak hold circuit 52 and an inverting buffer 53. The outputs of the peak hold circuit 52 and the inverting buffer 53 are connected to an addition circuit 54, whose output is supplied to a low-pass filter 55. The output thereof is connected to a peak hold circuit 56 and a division unit 57. The output of the peak hold circuit 56 is supplied through a sample hold circuit 58 to an A/D converter 59.

The A/D converter 59 is connected, through a bus line, to an I/O interface 60, a memory 61, an MPU 62 and a D/A converter 63, and the output of the D/A converter 63 is connected to a differentiation circuit 64, and, through a zero-cross comparison unit 65, to a vessel position calculating unit 66, which also receives the output of the I/O interface 60 and whose output is connected through a galvanometric mirror control unit 67 to the galvanometric mirror 22.

Also, the output of a clock pulse generator 68 is connected to the MPU 62 and a timing generator 69, whose output is connected to the one-dimensional CCD 42, the sample hold circuits 51, 58, the peak hold circuits 52, 56 and the division unit 57. Also, the output of the I/O interface 60 is connected to the optical path switching mirror 34, and the output of an input unit 70 is connected to the I/O interface 60. A movable mask drive circuit 84 is connected to a movable mask 82.

A vessel region extracting unit is constituted by the amplifier 50, sample hold circuits 51, 58, peak hold circuits 52, 56, inverting buffer 53, addition circuit 54, division unit 57 and differentiation circuit 64, and an AGC (automatic gain control) unit 72 is constituted by the peak hold circuit 56, the division unit 57 and the sample hold circuit 58. Also, a process condition determination unit 73 is constituted by the A/D converter 59, the I/O interface 60, the memory 61, the MPU 62 and the D/A converter 63, and an auto tracking control unit 74 is constituted by the zero-cross comparison unit 65, the vessel position calculation unit 66, and the galvanometric mirror control unit 67.

Figure 16:
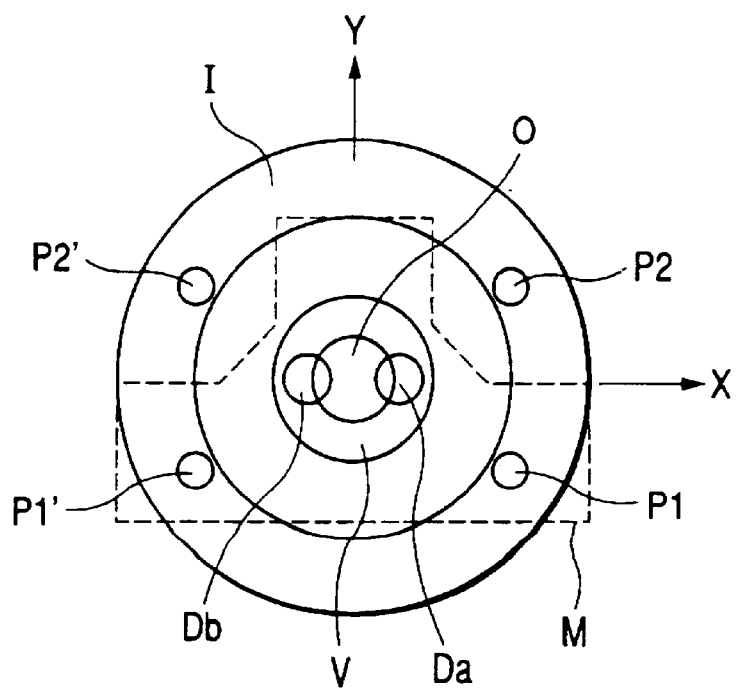
FIG. 16 is a schematic view showing the arrangement of optical beams on an pupil Ep.

FIG. 16 shows the arrangement of the light beams on the pupil Ep of the eye to be examined E, including an area I illuminated with the yellow illuminating light and corresponding to an image of the ring slit 5, an eye fundus observing light beam O showing an image of the aperture of the holed mirror 11, a measuring/received light beam V showing an image of the effective area of the upper and lower reflective faces of the galvanometric mirror 22, and two received measuring light beams Da, Db showing images of the paired mirrors 45a, 45b. There are also shown entrance positions P2, P2' of the measuring light, selected by the switching of the optical path switching mirror 34, and a chain-lined area M indicating an image of the lower reflective face 22a of the galvanometric mirror 22.

The white light emitted from the observing light source 1 is transmitted by the condenser lens 3. Then, light of yellow wavelength region only is transmitted by the field lens 4 with the band-pass filter, is further transmitted by the ring slit 5, the light shield member 6 and the relay lens 7, illuminates the transmissive liquid crystal panel 8 from the rear side, is further transmitted by the relay lens 9 and the light shield member 10, and is reflected by the holed mirror 11. Thus, light of the yellow wavelength region only is transmitted by the band-pass mirror 12 and the objective lens 2 and is focused as an image I of the eye fundus illuminating light beam on the pupil Ep of the eye to be examined E, thus uniformly illuminating the eye fundus Ea.

In this state, the transmissive liquid crystal panel 8 displays a fixation target which is projected by the illuminating light onto the eye fundus Ea of the eye to be examined E and is presented thereto as an fixation target image. The light shield members 6, 10 serve to separate the eye fundus illuminating light and the eye fundus observing light at the front eye region of the eye to be examined E, and the shape of these components is not critical as long as a suitable light shielding area can be formed.

The light reflected by the eye fundus Ea returns on the same optical path and is taken out, from the pupil Ep, as an eye fundus observing light beam, which is guided through the central hole of the holed mirror 11, the focusing lens 13 and the relay lens 14, is then focused as an eye fundus image Ea' by the scale plate 15 and reaches the optical path switching mirror 16.

When the optical path switching mirror 16 is retracted from the optical path, the observing eye e can observe the eye fundus image Ea' through the eye piece lens 17, but, when the optical path switching mirror 16 is inserted into the optical path, the eye fundus image Ea' focused on the scale plate 15 is refocused on the CCD camera 19 through the television relay lens 18 and is displayed on the liquid crystal monitor 20. The alignment of the apparatus is made under the observation of the eye fundus image Ea' either through the eyepiece lens 17 or the liquid crystal monitor 20.

The measuring light, emitted from the laser diode 36, is collimated by the collimating lens 35 and, if the optical path switching mirror 34 is inserted in the optical path, is reflected by this mirror 34 and the fixed mirror 33 to pass through the lower part of condenser lens 30, but, if the optical path switching mirror 34 is retracted from the optical path, it directly passes through the upper part of condenser lens 30, thus being transmitted by the dichroic mirror 29.

On the other hand, the tracking light emitted from the tracking light source 38 is expanded in beam diameter with different magnifications in the vertical and horizontal directions by the beam expander 37, then is reflected by the mirror 32, is shaped into a desired shape by the shaping mask 31, is further reflected by the dichroic mirror 29 and is superposed by the condenser lens 30 with the measuring light, which is focused into a spot at a position conjugate with the center of the aperture of the mask 31.

The measuring light and the tracking light mutually superposed are transmitted by the lens 24, reflected by the upper reflective face 22b of the galvanometric mirror 22, transmitted by the black spot plate 27, reflected by the concave mirror 28, again transmitted by the black spot plate 27 and the optical path length correcting semicircular plate 26, and are returned toward the galvanometric mirror 22.

By the function of the relay optical system, which is positioned above the galvanometric mirror 22 and which forms the image of the upper reflective face 22b and the lower reflective face 22a of the galvanometric mirror 22 with a magnification of −1, the measuring light and the tracking light, reflected at either position P or P' located as shown in FIG. 16 at the rear side of the image M of the dichroic mirror 22, are returned to a position P2 or P2' corresponding to the recessed portion of the galvanometric mirror 22, thus being directed to the image rotator 21 without being reflected by the galvanometric mirror 22. After passing the image rotator 21, the measuring light and the tracking light are deflected by the band-pass filter 12 toward the objective lens 2 and projected onto the eye fundus Ea of the eye to be examined E.

Thus, the measuring light and the tracking light are reflected by the upper reflective face 22b of the galvanometric mirror 22, and, in the returning path, they enter the galvanometric mirror 22 in a state deviated from the optical axis of the objective lens 2, whereby these lights are focused as a spot image P2 or P2' on the pupil Ep as shown in FIG. 3 and illuminate the eye fundus Ea in a spot shape.

The light scattered and reflected at the eye fundus Ea is condensed by the objective lens 2, is then reflected by the band-pass filter 12, transmitted by the image rotator 21, reflected by the lower reflective face 22a of the galvanometric mirror 22, and transmitted by the second focusing lens 23, and the measuring light and the tracking light are separated by the dichroic mirror 39. The tracking light is transmitted by the dichroic mirror 39, and is focused by the field lens 40 and the imaging lens 41 on the one-dimensional CCD 42.

A part of the measuring and tracking lights scattered and reflected on the eye fundus Ea is transmitted by the bandpass mirror 32 and guided to the eye fundus observing optical system positioned behind the holed mirror 11, wherein the tracking light is focused on the scale plate 15 as a rod-shaped indicator T, while the measuring light is focused as a spot at the center of the indicator T. These images can be observed, together with the eye fundus image Ea' and the fixation target image, through the eyepiece lens 17 or the liquid crystal monitor 20. In this state, an unrepresented spot image is superposed at the center of the indicator T, which can be moved one-dimensionally on the eye fundus Ea by an operation member, such as the operation rod of the input unit 70.

At first the examiner executes focusing of the eye fundus image Ea'. By the adjustment of a focusing knob of the input means 70, the transmissive liquid crystal panel 8, the focusing lenses 13, 23 and the focusing unit 25 are moved in mutual linkage, by unrepresented drive means, along the optical axis. When the eye fundus image Ea' is focused, all the transmissive liquid crystal panel 8, the scale plate 15, the one-dimensional CCD 42 and the confocal diaphragm 44 become conjugate with the eye fundus Ea. Observing the focus state on the eye fundus image Ea', the examiner sets the depth of the vessel Ev to be measured, and executes focusing of the eye fundus image Ea'.

After the focusing operation, the examiner changes the observation area by guiding the visual axis of the eye to be examined E, and manipulates the input unit 70 to move the target vessel Ev to a suitable position. The system control unit 47 drives a control circuit for controlling the transmissive liquid crystal panel 8 to move the fixation target image. Then, the examiner manipulates the operation rod of the input unit 70 to rotate the indicator T in such a manner that it becomes perpendicular to the longitudinal direction of the target vessel Ev. The system control unit 47 drives a control circuit for controlling the image rotator 21, thereby driving the image rotator 21 and rotating the indicator T.

After confirming the tracking, the examiner presses in the measuring switch of the input unit 70 to initiate the measurement. The measuring light is reflected by the dichroic mirror 39, is then transmitted through the aperture of the confocal diaphragm 44, is reflected by the paired mirrors 45a, 45b and is received by the photomultipliers 46a, 46b, whose outputs are supplied to the system control unit 47 and are subjected to frequency analysis to determine the blood flow velocity on the eye fundus Ea.

Figure 17:
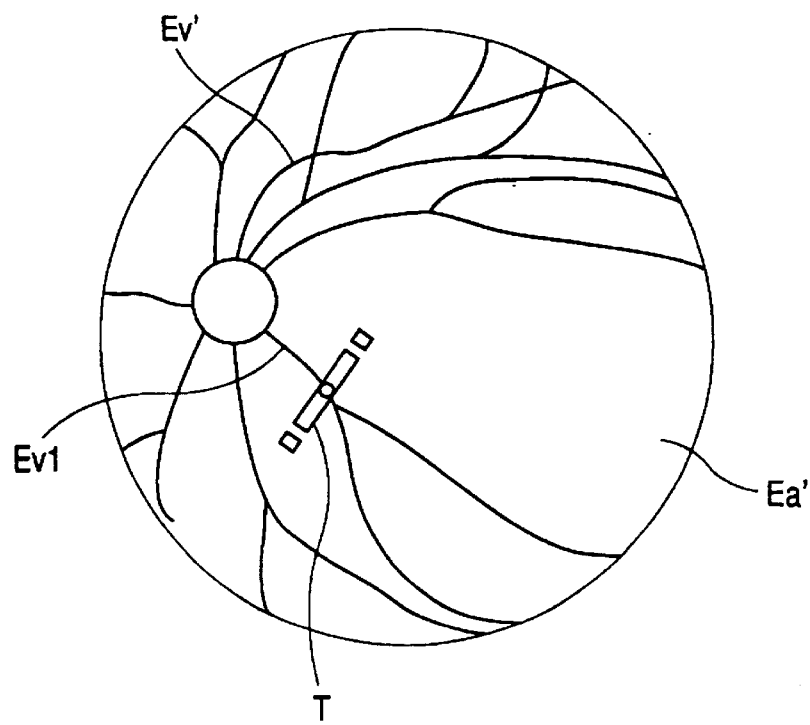
FIG. 17 is a schematic view showing the image of an observed eye fundus.

In case vessels Ev are absent around the vessel Ev1 to be tracked as shown in FIG. 17, in response to the start of the tracking operation by the examiner, the vessel image Ev' taken by the one-dimensional CCD 42 is read at a timing generated by the timing generator 69 and is amplified by the amplifier 50. The output signal thereof is subjected to sample holding in the sample hold circuit 51 at a timing generated by the timing generator 69. Since the portion of the vessel Ev is dark while the surrounding area is light, the output signal assumes a form as shown in FIG. 18D, wherein a portion of the high output level indicates a light region.

The output signal of the sample hold circuit 51 is entered into the peak hold circuit 52, which executes peak holding only during an L-level period generated by the timing generator 69 as shown in FIG. 18A, but merely transmits the input signal in other periods. The output of the peak hold circuit 52 and a signal obtained by inverting, by the inverting buffer 53, the output of the sample hold circuit 51 are supplied to and added in the addition circuit 54 whereby a vessel image signal alone is extracted as shown in FIG. 18E. The output of the addition circuit 54 is supplied to the low-pass filter 55 to eliminate the high frequency components as shown in FIG. 18G.

The output of the low-pass filter is supplied to the peak hold circuit 56, which executes peak holding only during an L-level period, as shown in FIG. 18B, for supply to the sample hold circuit 58. The sample hold circuit 58 executes a sampling operation in an L-level period as shown in FIG. 18C and a holding operation in an H-level period. The output signal of the sample hold circuit 58 is shown, together with the output signal of the low-pass filter 55, in FIG. 18F, and enters into the A/D converter 59 for conversion into digital data, which are processed in the MPU 62 and released from the D/A converter 63 as an AGC gain for vessel position detection in the next sampling cycle.

FIGS. 18A to 18I show the signal wave forms in case the signal level entered from the MPU 62 to the A/D converter 59 is set to the D/A converter 63. The output wave form thereof is supplied as the AGC gain for the vessel position detection while that of the low-pass filter 55 is supplied as the tracking signal, to the division unit 57, which executes a calculation (output signal of low-pass filter 55)÷(output signal of D/A converter 63) and executes auto gain control for the vessel position detection by the sampling of a period A on the signal of the vessel to be tracked.

The output signal, shown in FIG. 18H, of the division unit 57 is differentiated by the differentiation circuit 64, whose output is entered into the zero-cross comparison unit 65 and is compared therein with ca. 0 V. The obtained signal is outputted as the vessel position signal shown in FIG. 18I. This vessel position signal is compared, in the vessel position calculation unit 66, with a tracking center position signal outputted from the I/O interface 60, thereby outputting the amount of displacement of the vessel closest to the center of tracking, to the galvanometric mirror control unit 67, which in response drives the galvanometric mirror 22 so as to compensate for this amount of displacement.

Figure 19:
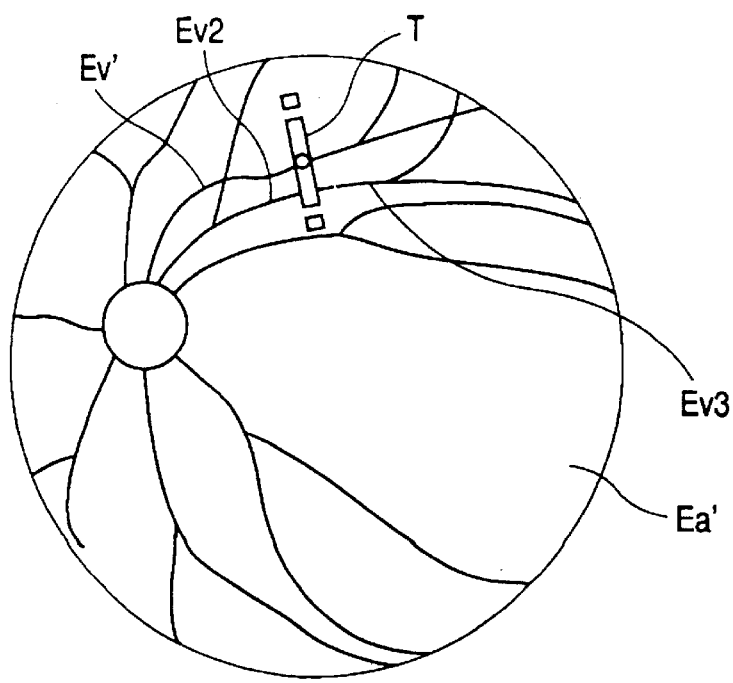
FIG. 19 is a schematic view showing the image of an observed eye fundus.

In the following there will be explained, with reference to output wave forms shown in FIGS. 20A to 20I, a case where a vessel Ev3 of a higher contrast is present around a vessel Ev2 to be tracked, as shown in FIG. 19. If the signal level entered from the MPU 62 to the A/D converter 59 is entered, without change, to the D/A converter 63, the displacement amount d from the tracking center of the vessel Ev2 is smaller than the displacement amount d' from the tracking center of the vessel Ev3 in a sampling cycle n=0, so that the vessel position calculation unit 66 outputs the displacement amount d of the vessel closest to the tracking center, to the galvanometric mirror control unit 67, which drives the galvanometric mirror 22 so as to compensate for this displacement amount d, whereby, in a sampling cycle n=1, the image of the vessel Ev2 is taken at the approximate center of tracking.

In a sampling cycle n=1, however, the AGC for the vessel position detection is controlled with a gain based on the vessel Ev3, whereby the signal of the vessel Ev2 is normalized to a small value as shown in FIG. 20H and the output of the zero-cross comparison unit 65 becomes unstable. On the other hand, the image signal of the vessel Ev3 is given an appropriate AGC, whereby the output of the zero-cross comparison unit 65 becomes stable. Consequently, the vessel position calculation unit 66 may judge the vessel position signal of the vessel Ev3 as the displacement amount of the vessel closest to the tracking center, whereby the tracking operation may be applied to the vessel Ev3.

Figure 21:
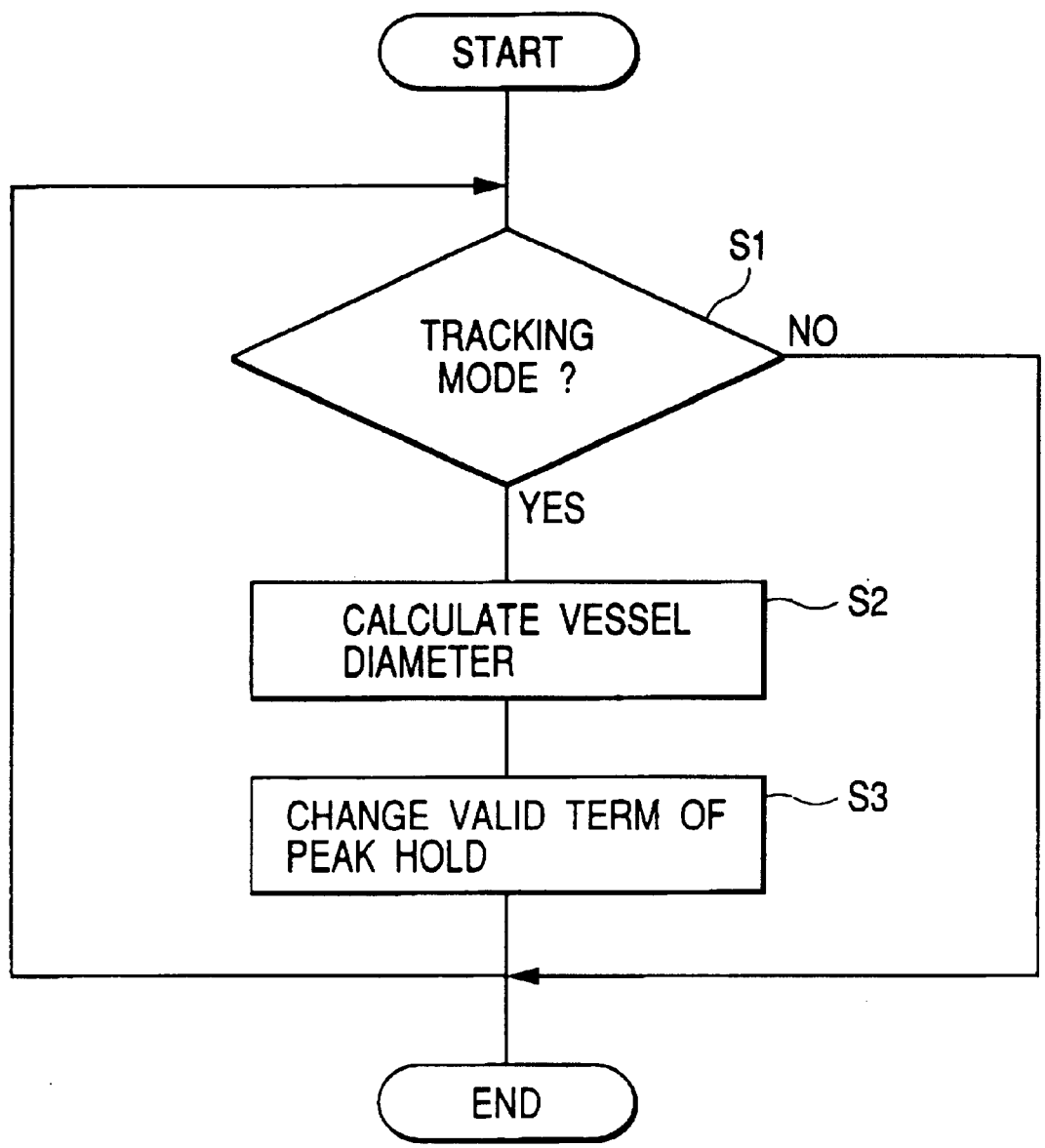
FIG. 21 is a flow chart.
Figure 22:
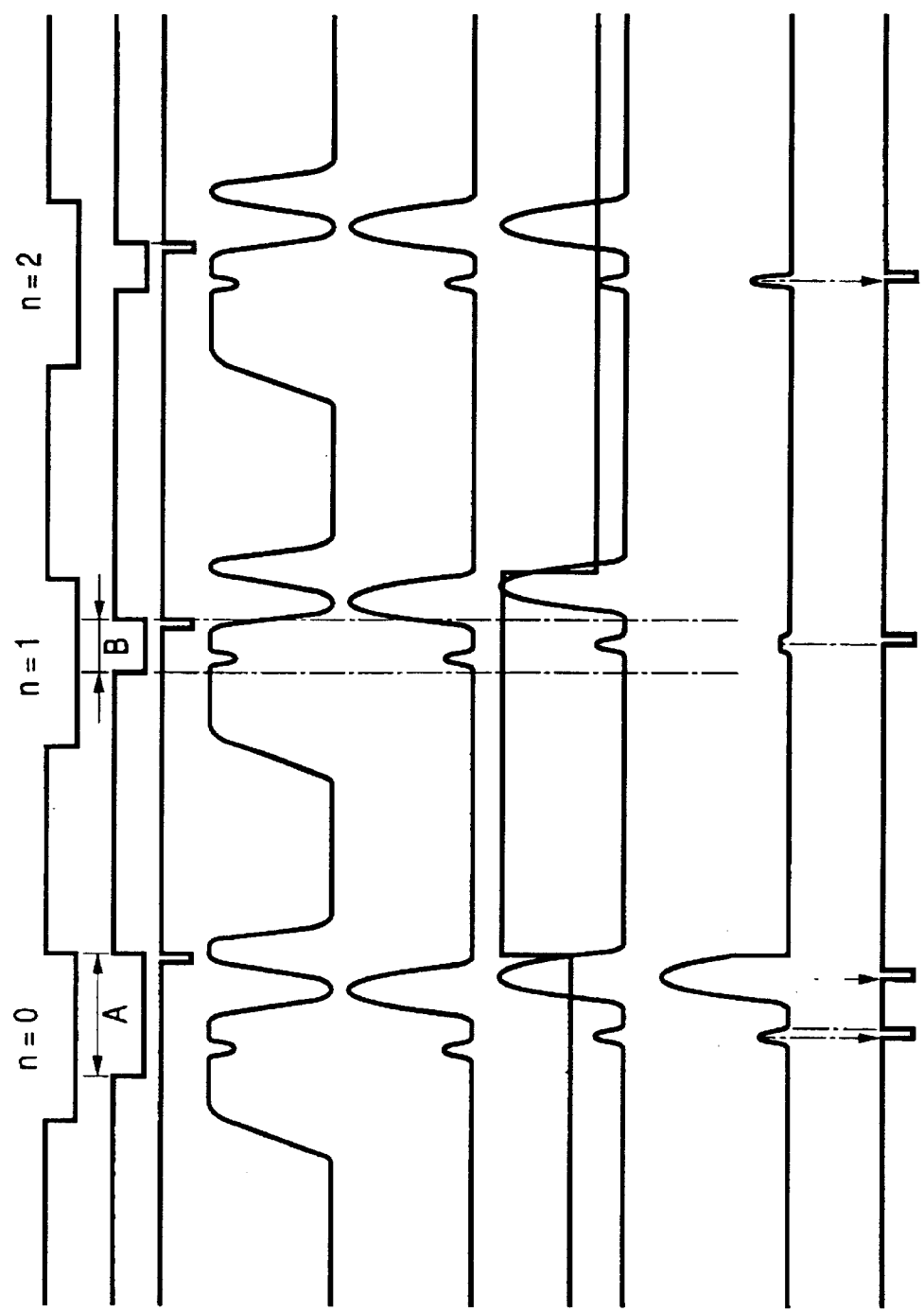
FIGS. 22A, 22B, 22C, 22D, 22E, 22F, 22G, 22H and 22I and FIGS. 23A, 23B, 23C, 23D, 23E, 23F, 23G, 23H, 23I and 23J are timing charts showing a tracking signal.

In order to prevent such phenomenon, the MPU 62 executes a process according to a flow chart shown in FIG. 21. A step SI discriminates if the tracking mode is selected, and, if selected, a step S2 executes conversion of the image signal from the sample hold circuit 51 into digital data, then executes wave form analysis by the MPU 62 and calculates the diameter of the vessel closest to the tracking center in the sampling cycle n=0.

Then, in a step S3, the MPU 62 outputs a signal for varying according to the thus calculated vessel diameter, the peak hold period of the peak hold circuit 56, indicating the effective AGC range of the AGC unit 72 for the vessel position detection, to the timing generator 69 through the I/O interface 60, thereby varying the peak hold period from A to B as shown in FIGS. 22A to 22I. In the present embodiment, the effective AGC range for the vessel position detection is so varied that the peak hold period becomes about twice that of the vessel diameter.

Figure 23:
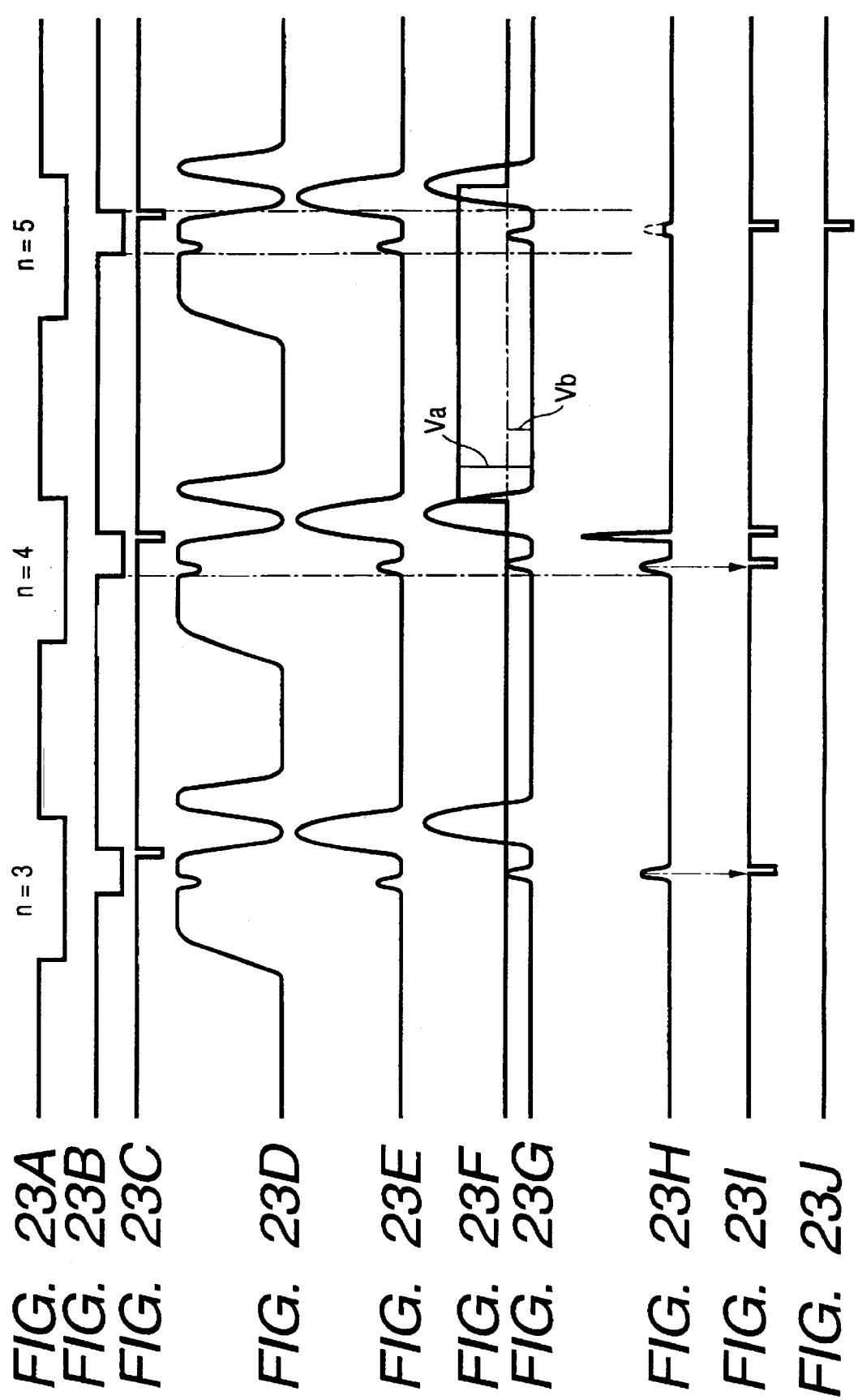

FIGS. 23A to 23J show the wave forms in the sampling cycles n=3 to 5, succeeding to the sampling cycle n=2 shown in FIGS. 22A to 22I. FIGS. 23A to 23J show a case in which the tracking is disturbed by an external perturbation in the sampling cycle n=4, and the image signal of the vessel Ev3 is introduced in the effective AGC range for the vessel position detection, namely in the period B. In the sampling cycle n=4, as shown in FIG. 23G, a part of the image signal of the vessel Ev3 is retained by the sample hold circuit 58, and entered into the A/D converter 59, whereby the AGC gain for the vessel position detection in the sampling cycle n=5 is outputted from the D/A converter 63. The AGC gain for the vessel position detection in the sampling cycle n=5 assumes a value I/Va, which is smaller than the gain I/Vb required for applying appropriate AGC to the vessel Ev2, so that the output signal for the vessel Ev2 from the zero-cross comparison unit 65 becomes unstable as shown in FIG. 23I.

Figure 24:
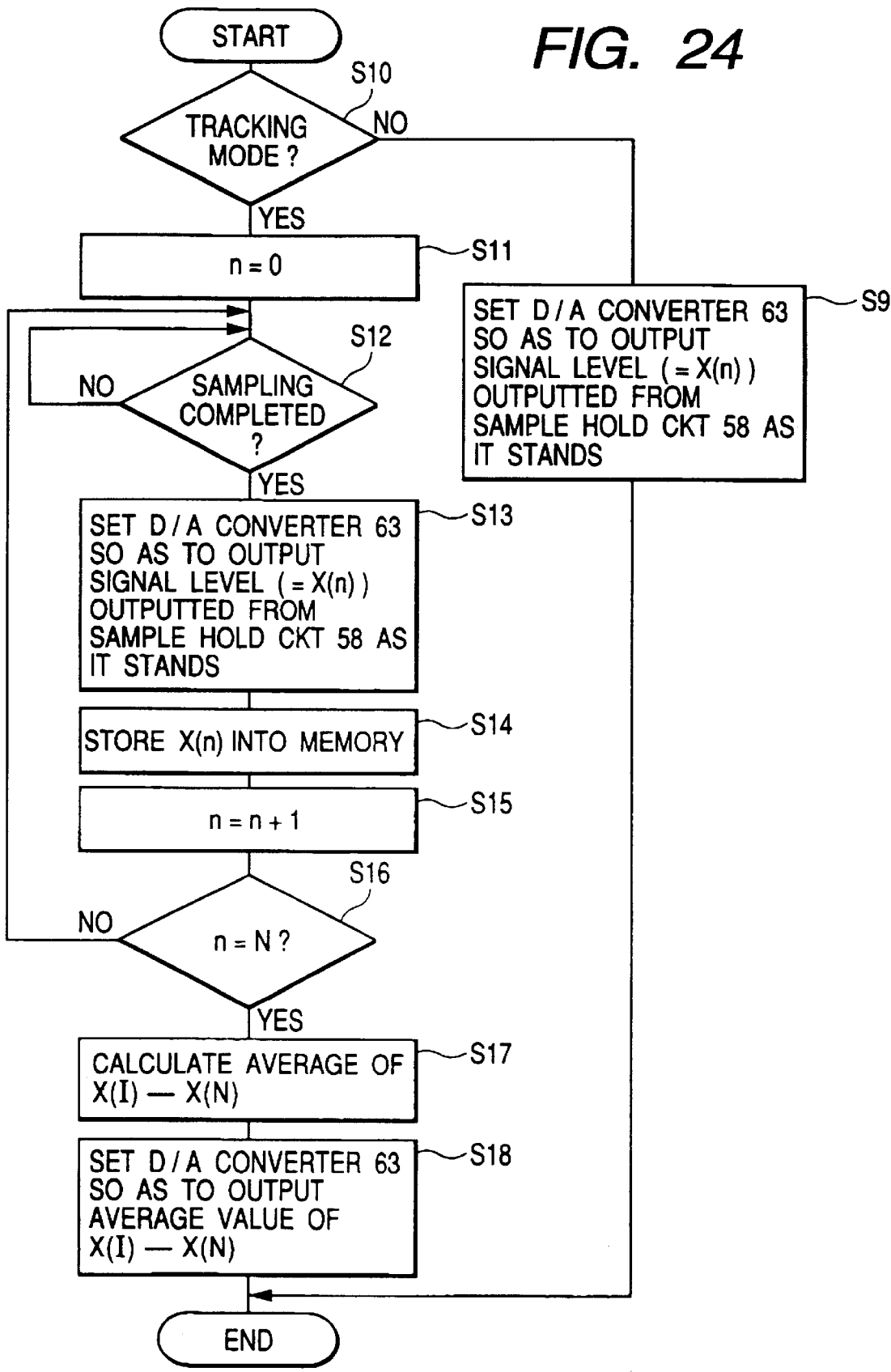
FIG. 24 is a flow chart.

Therefore, the MPU 62 executes a process according to a flow chart shown in FIG. 24. A step S10 discriminates whether the tracking mode is selected, and, if selected, a step S11 resets a counter for determining the number of samplings of the signal level outputted from the sample hold circuit 58. If the number of samplings does not exceed a predetermined value, a step S12 discriminates whether the sampling operation of the sample hold circuit 58 has been terminated, and, if terminated, a step S13 so sets the D/A converter 63 that the output signal of the sample hold circuit 58 is outputted without change, and a step S14 stores the output signal level of the sample hold circuit 58 in the memory 61. If steps S15, S16 identify that the number of samplings has reached a predetermined value, a step S17 calculates the average of the output signals from the sample hold circuit 58 and a step S18 so sets the D/A converter 63 as to output such an average value.

In the present embodiment, the predetermined value is selected as n=3, and, in the sampling cycles n=0 to n=3, the output signal of the sample hold circuit 58 is outputted without change, as shown in FIGS. 22A to 22I and 23A to 23J, for applying AGC for the vessel position detection. In the sampling cycle n=4 or subsequent cycles, the AGC gain supplied to the division unit 57 is fixed at I/Vb, which is an average of the sampling cycles n=1 to n=3. Even if the tracking is disturbed by an external perturbation in the sampling cycle n=4 to include the image signal of the vessel Ev3 in the effective AGC range for the vessel position detection, namely in the period B, the output signal for the vessel Ev2 from the zero-cross comparison unit 65 in the sampling cycle n=5 is stabilized as shown in FIG. 23J so that the tracking operation becomes stable.

Figure 25:
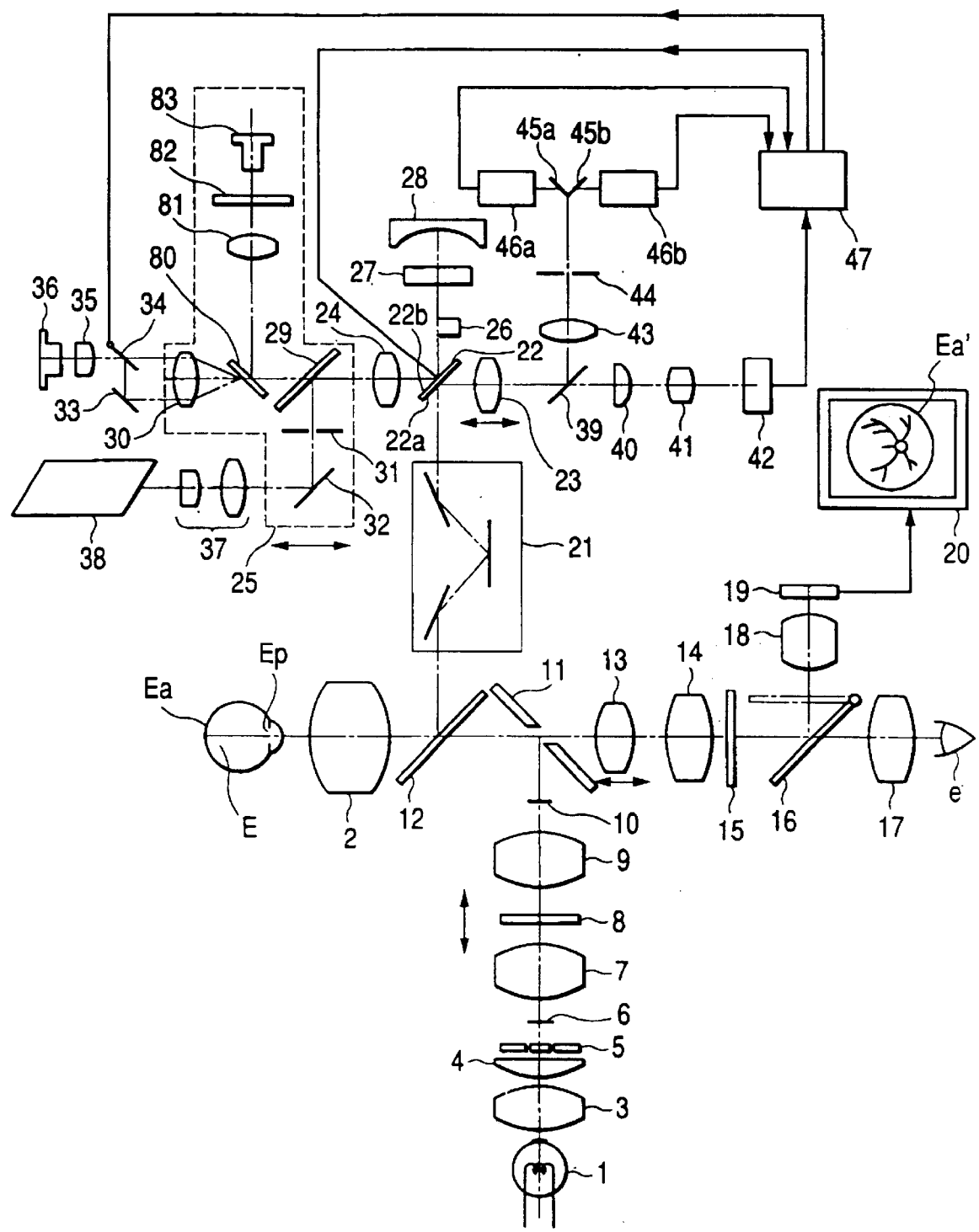
FIG. 25 is a view showing another embodiment.

FIG. 25 shows another embodiment, which is different from the first embodiment in that, in the focusing unit 25, a half mirror 80 is provided between the dichroic mirror 29 and the condenser lens 30 and that, at the entrance side of the half mirror 80, there are provided a relay lens 81, a movable mask 82 provided in a position substantially conjugate with the mask 31 and indicating the AGC range for the vessel position detection, and an LED light source 83 emitting red light. Also, the output of the I/O interface 60 of the process condition determination unit 73 shown in FIG. 15 is supplied to a movable mask drive circuit 84 for controlling the movable mask 82. Other configurations are same as those in the first embodiment, and components equivalent to those in the first embodiment are indicated by the same numbers therein.

Figure 26:
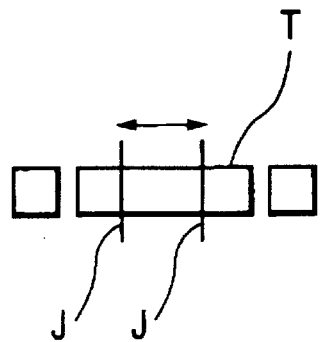
FIG. 26 is an elevation view of a tracking index.

An image of the movable mask 82 is projected, as an index mark J as shown in FIG. 26, onto the eye fundus Ea of the eye to be examined E. This index mark J indicates the effective AGC range for the vessel position detection.

Figure 27:
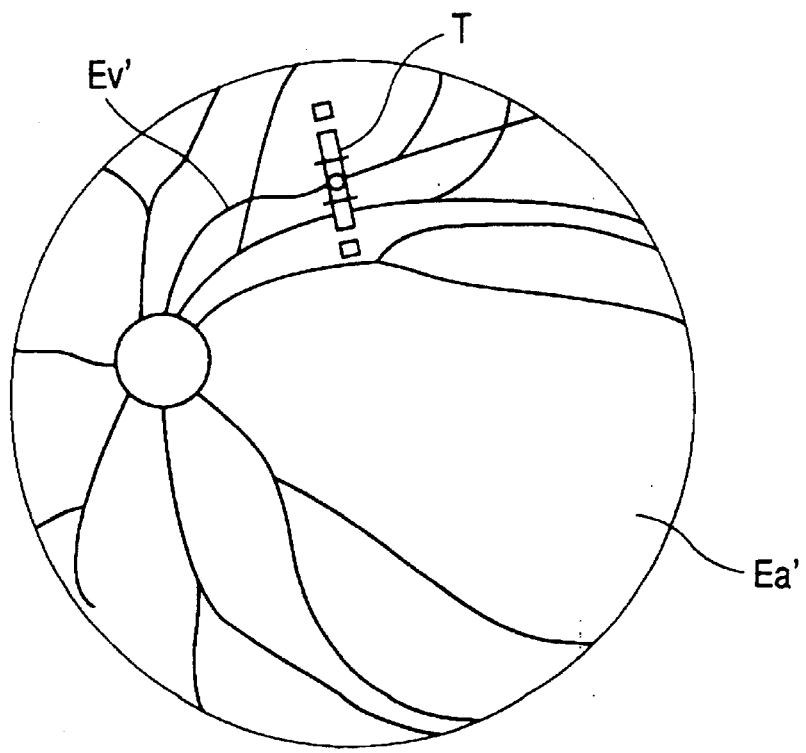
FIG. 27 is a schematic view showing the image of an observed eye fundus.

The examiner observes the state of the eye fundus image Ev' shown in FIG. 27, and, if the tracking operation is judged difficult, for example, because the vessel to be tracked has a low contrast or is thin, the examiner manipulates the input unit 70 to manually change the effective AGC range for the tracking operation. This information is supplied through the I/O interface 60 to the MPU 62, which in response varies the peak hold period of the peak hold circuit 56, representing the effective AGC range for the vessel position detection, thereby controlling the movable mask drive circuit 84 to move the movable mask 82, whereby the index mark J or the image of the movable mask 82 is moved, as indicated by an arrow in FIG. 26.

Also, in case of an automatic change of the AGC range of the tracking operation in the first embodiment, the index mark J may be projected onto the eye fundus Ea of the eye to be examined E. In this case the index mark J moves in linkage with the AGC range of the tracking operation. It is also possible to combine the configuration of the first embodiment for automatic change and that of the second embodiment for manual change.

As explained in the foregoing, the ophthalmic inspecting apparatus of the present invention is capable of executing an AGC process for the vessel position detection in a range narrower than the effective range of the tracking light and a wave form processing for normalizing the vessel image signal, by determining the processing condition based on the signal in the vicinity of the specified region and extracting the specified region for automatic tracking, whereby the tracking operation can be achieved in a stable manner on a thin vessel.

Also, the ophthalmic inspecting apparatus of the present invention is capable, by determining the processing condition based on the signal in the vicinity of the specified region, displaying the result on display means and extracting the specified region for automatic tracking, of varying the effective AGC range for the vessel position detection in the tracking operation of the vessel in the eye to be examined, whereby the tracking operation can be achieved in a stable manner even on a vessel of a lower contrast when two vessels are positioned mutually close.

What is claimed is:

1. An ophthalmic apparatus comprising:
   an illuminator illuminating an eye fundus of an eye to be examined with a light;
   a detector receiving reflected light from the illuminated eye fundus;
   a gain controller automatically setting an optimum gain of said detector on the basis of an output signal of said detector; and
   a system that controls the detector and the gain controller so as to set the optimum gain of said detector for a desired portion of the eye fundus, then to obtain output signals of said detector while keeping the set optimum gain unchanged during at least one of a measurement and a tracking operation at the desired portion.

2. An ophthalmic apparatus according to claim 1, wherein said eye fundus comprises a blood vessel and said detector comprises an image sensor to obtain blood vessel images.

3. An ophthalmic apparatus according to claim 1, wherein said eye fundus comprises a blood vessel, said illuminator comprises a laser light source, and said detector detects scattered light from the blood vessel to measure blood flow.

4. An ophthalmic apparatus according to claim 3, wherein said detector comprises a photomultiplier.

5. An ophthalmic apparatus according to claim 1, further comprising an automatic tracking system for tracking movement of the eye based on the obtained signals, wherein said illuminator comprises a laser light source for the tracking.

6. An ophthalmic apparatus according to claim 5, further comprising a start switch, wherein said gain controller sets the optimum gain in response to the operation of said start switch.

7. An ophthalmic measuring method comprising the steps of:
   illuminating an eye to be examined with a light;
   receiving, with a detector, reflected light from the illuminated eye;
   setting an optimum gain of said detector for a desired portion on the eye fundus on the basis of an output signal of said detector; and
   obtaining output signals of said detector keeping the set optimum gain unchanged during at least one of a measurement and a tracking operation at the desired portion.

8. A method according to claim 7, further comprising a step of measuring blood flow of a blood vessel on the eye fundus.

9. A method according to claim 7, further comprising a step of executing automatic tracking to follow movement of the eye.

* * * * *

UNITED STATES PATENT AND TRADEMARK OFFICE
CERTIFICATE OF CORRECTION

PATENT NO. : 6,337,993 B1
DATED : January 8, 2002
INVENTOR(S) : Nobuyoshi Kishida et al.

It is certified that error appears in the above-identified patent and that said Letters Patent is hereby corrected as shown below:

Title page,
Item [57], ABSTRACT,
Line 7, "unit" should read -- units --.
Line 8, "units" should read -- unit --.

Column 1,
Line 54, "such" should read -- such an --.

Column 3,
Line 20, ":in" should read -- in --.
Line 28, "an" should read -- a --.
Line 53, "a" should be deleted.

Column 4,
Line 3, "as" should read -- as a --.
Line 67, "coherent, light" should read -- coherent light, --.

Column 5,
Line 19, "a" should read -- the --.

Column 6,
Line 30, "in." should read -- in --.

Column 8,
Line 66, "maintained" should read -- is maintained --.

Column 9,
Line 31, "a long as" should read -- long as a --; and
Line 34, "s tart" should read -- start --.

Column 11,
Line 42, "is" should read -- are --.

Column 12,
Line 36, "an " should read -- a --.
Line 66, "other" should read -- the other --.
Line 67, "the" (1st occurrence) should be deleted.

UNITED STATES PATENT AND TRADEMARK OFFICE
CERTIFICATE OF CORRECTION

PATENT NO.    : 6,337,993 B1
DATED         : January 8, 2002
INVENTOR(S)   : Nobuyoshi Kishida et al.

It is certified that error appears in the above-identified patent and that said Letters Patent is hereby corrected as shown below:

<u>Column 13,</u>
Line 25, "light, which are" should read -- light --; and "light" (2$^{nd}$ occurrence) should read -- light, which are --.
Line 46, "the" should be deleted.

<u>Column 14,</u>
Line 52, "an such" should read -- such an --.

<u>Column 15,</u>
Line 61, "there" should read -- it --.

<u>Column 18,</u>
Line 54, "in" should read -- in a --.

<u>Column 20,</u>
Line 43, "an" should read -- a --.

<u>Column 24,</u>
Line 37, "221" should read -- 22I --.
Line 60, "same" should read -- the same --.

Signed and Sealed this

Eleventh Day of March, 2003

JAMES E. ROGAN
*Director of the United States Patent and Trademark Office*